US005686242A

United States Patent [19]
Bruice et al.

[11] Patent Number: 5,686,242
[45] Date of Patent: Nov. 11, 1997

[54] DETERMINATION OF OLIGONUCLEOTIDES FOR THERAPEUTICS, DIAGNOSTICS AND RESEARCH REAGENTS

[75] Inventors: Thomas W. Bruice, Carlsbad; Walter F. Lima, San Diego, both of Calif.

[73] Assignee: ISIS Pharmaceuticals, Inc., Carlsbad, Calif.

[21] Appl. No.: 330,000

[22] Filed: Oct. 27, 1994

Related U.S. Application Data

[63] Continuation-in-part of Ser. No. 755,485, Sep. 5, 1991, abandoned.

[51] Int. Cl.$^6$ .......................... C12Q 1/68; G01N 33/53; C07H 21/00
[52] U.S. Cl. .......................... 435/6; 435/7.1; 536/23.1; 536/25.3
[58] Field of Search .......................... 435/6, 7.1; 536/23.1, 536/25.3

[56] References Cited

U.S. PATENT DOCUMENTS

| | | | |
|---|---|---|---|
| 4,935,357 | 6/1990 | Szybalski | 435/91.53 |
| 5,010,175 | 4/1991 | Rutter et al. | 530/334 |
| 5,475,096 | 12/1995 | Gold et al. | 536/23.1 |

FOREIGN PATENT DOCUMENTS

WO 92/00091  9/1992  WIPO.

OTHER PUBLICATIONS

Frohman et al. Rapid production of full–length cDNAs from rare transcripts: amplification using a single gene–specific oligonucleotide primer. Proc. Natl. Acad. Sci. USA vol. 85 pp. 8998–9002 1988.

Promega Catalog 1993/1994 p. 58 1993.

Brenowitz et al. Quantitative DNase fpptprint titration: A method for studying protein–DNA interactions Methods in Enzymology vol. 130 132–181 1986.

Tullius et al. Hydroxy radical footprinting: A high–resolution method for mapping protein–DNA contacts Methods in Enzymology vol. 155 537–558 1987.

Hasegawa et al. Genomic divergence of HIV-2 from Ghana AIDS Research and Human Retroviruses vol. 5 593–604 1989.

Sekiya et al. Molecular cloning and the total nucleotide sequence of the heman c–Ha–ras–1 gene activated in a melanoma from a Japanese patient Proc. Natl. Acad. Sci. USA vol. 81 4771–4775 1984.

Kato et al. Molecular cloning of the human hepatitis C virus genome from Japanese patients with non–A, non–B hepatitis Proc. Natl. Acad. Sci. USA vol. 87 9524–9528 1990.

Musso et al. Construction and characterization of versatile kanamycin–resistance cassettes derived from the Tn5 transposon Gene vol. 85 205–207 1989.

Xu et al. The PRP4 (RNA4) protein of *Saccharomyces cerevisiae* is associated withthe 5' portion of the U4 small nuclear RNA Molecualr and Cellular Biology vol. 10 1217–1225 1990.

Blackwell et al., "Differences and Similarities in DNA–Binding Preferences of MyoD and E2A Protein Complexes Revealed by Binding Site Selection", *Science* 250: 1104–1110 (1990).

Blackwell et al., "Sequence–Specific DNA Binding by the c–Myc Protein", Science 250: 1149–1151 (1990).

Bock et al., "Selection of Single–Stranded DNA Molecules that Bind and Inhibit Human Thrombin", Nature 355:564–566 (1992).

Carchon et al., "Capillary electrophoresis", *Amer. Biotech. Lab.* 1992, 67–72.

Chittenden et al., "The T/E1A–Binding Domain of the Retinoglastoma Product Can Interact Selectively with a Sequence–Specific DNA–Binding Protien", Cell 65:1073–1082 (1991).

Cobb and Novotny, "Peptide Mapping of Complex proteins at the Low–Picomole Level with Capillary Electrophoretic Separations" *Anal. Chem.* 64: 879–886 (1992).

Dooley and Houghten, "The Use of Positional Scanning Synthetic Peptide Combinatorial Libraries for the Rapid Determination of Opioid Receptor Ligands" *Life Sciences*, 1993, 52, 1509–1517.

Dooley, et al., "Acetalins: Opioid Receptor Antagonists Determined Through the Use of Synthetic Peptide Combinatorial Libraries" *Proc. Natl. Acad. Sci. U.S.A.,* 1993, 90, 10811–10815.

Dvoretzky et al., "A Quantitative in Vitro Focus Assay for Bovine Papilloma Virus" Virology 103: 369–375 (1980).

Ellington & Szostak, "In Vitro Selection of RNA Molecules That Bind Specific Ligands" Nature 346: 818–822 (1990).

Fodor et al., "Light–Directed, Spatially Addressable Parallel Chemical Synthesis" Science 251: 767–773 (1991).

Geysen et al., "A Priori Delineation of A Peptide Which Mimics a Discontinuous Antigenic Determinant" Molec. Immunology 23: 709–715 (1986).

Gorman et al., "Recombinant Genomes Which Express Chloramphenicol Acetyltransferase in Mammalian Cells" Molec. & Cellular Biology 2: 1044–1051 (1982).

Graham and Van Der Eb, "A New Technique for the Assay of Infectivity of Human Adenovirus 5 DNA" Virology 52: 456–467 (1973).

Groger et al., "Directional Antisense and Sense cDNA Cloning Using Epstein–Barr Virus Episomal Expression Vectors" Gene 81: 285–294 (1989).

Houghten et al., "Generation and Use of Synthetic Peptide Combinatorial Libraries for Basis Research and Drug Discovery" Nature 354: 84–86 (1991).

(List continued on next page.)

Primary Examiner—James Ketter
Assistant Examiner—John S. Brusca
Attorney, Agent, or Firm—Woodcock Washburn Kurtz Mackiewicz & Norris LLP

[57] ABSTRACT

Oligonucleotides which selectively bind to target biomolecules are determined by in vitro assay of a pool of random oligonucleotides for activity against said biomolecules, followed by recovery and characterization of selected oligonucleotides. Oligonucleotides so determined may be utilized for therapeutic, diagnostic and research reagent purposes.

77 Claims, No Drawings

OTHER PUBLICATIONS

Henderson et al., "HLA–A2.1–Associated Peptides from a Mutant Cell Line: A Second Pathway of Antigen Presentation" *Science* 1992 255 1264–1266.

Hunt, et al., "Characterization of Peptides Bound to the Class I MHC Molecule HLA–A2.1 by Mass Spectrometry" *Science,* 1992, 255, 1261–1263.

Jayawickreme, Channa et al., "Creation and Functional Screening of a Multi–use Peptide Library" *Proc. Natl. Acad. Sci. U.S.A.,* 1994, 91, 1614–1618.

Jellinek, D. et al., "High–Affinity RNA Ligands to Basic Fibroblast Growth Factor Inhibit Receptor Binding" *Proc. Natl. Acad. Sci. U.S.A.,* 1993, 90, 11227–11231.

Jenison, Robert D. et al., "High–Resolution Molecular Discrimination by RNA" *Science,* 1994, 263, 1425–1429.

Joyce, "Amplification, Mutation and Selection of Catalytic RNA" Gene 82: 83–87 (1989).

Kinzler and Vogelstein, "Whole Genome PCR: Application to the Identification of Sequences Bound by Gene Regulatory Proteins", Nucleic Acids Res. 17: 3645–3653 (1989).

Kinzler and Vogelstein, "The GLI Gene Encodes a Nuclear Protein Which Binds Specific Sequences in the Human Genome" Molecular and Cellular Biology 10: 634–642 (1990).

Lam et al., "A New Type of Synthetic Peptide Library for Identifying Ligand–Binding Activity" Nature 354: 82–84 (1991).

Ohlmeyer et al., "Complex Synthetic Chemical Libraries Indexed with Molecular Tags" Proc. Natl. Acad. Sci. USA 90: 10922–10926 (1993).

Owens et al., "The Rapid Identification of HIV Protease Inhibitors Through the Synthesis and Screening of Defined Peptide Mixtures", Biochem & Biophys. Res. 181: 402–408 (1991).

Robertson and Joyce, "Selection in vitro of an RNA Enzyme That Specifically Cleaves Single–Stranded DNA" Nature 344 467–8 Mar. 29, 1990.

Rodriguez et al., "Capillary non–gel sieving electrophoresis of nucleic acids", *Amer. Biotech. Lab.* 1992, 21–22.

Schneider, Dan et al., "Selective Enrichment of RNA Species for Tight Binding to *Escherichia coli* rho Factor" *FASEB J.,* 1993, 7, 201–207.

Schneider, Dan et al., "Selection of High Affinity RNA Ligands to the Bacteriophage R17 Coat Protein" *J. Mol. Biol.,* 1992, 228, 862–869.

Stevenson, "HPCE '92: Will this kid amount to much?" *Amer. Lab,* 1992, 17–22.

Thiesen and Bach, "Target Detection Assay (TDA): A Versatile Procedure to Determine DNA Binding Sites as Demonstrated on SP1 Protein", Nuc. Acids Res 18: 3203–3209 (1990).

Toulas et al., "Applications of a Laser–Induced Fluorescence Detector for Capillary Electrophoresis to Measure Attomolar and Zeptomolar Amounts of Compounds" *LC–GC,* 1992, 10, 471–476.

Tuerk and Gold, "Systematic Evolution of Ligands by Exponential Enrichment: RNA Ligands to Bacteriophage T4 DNA Polymerase", Science 249: 505–510 (1990).

Zuckerman, Ronald N. et al., "Identification of Highest–Affinity Ligands by Affinity Selection from Equimolar Peptide Mixtures Generated by Robotic Synthesis" *Proc. Natl. Acad. Sci.* 1992, 89, 4505–4509.

Krieger et al., "Capillary electrophoresis" *Chem. and Engin. News,* 1992, 69–70.

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GGATGTTTTT TTTTTTT                                18

( 2 ) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CGCTGGATCC GCTTTTTTTT TTTTTTU                    27

( 2 ) INFORMATION FOR SEQ ID NO:3:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:3:

UUGCCCACAC                                              10

( 2 ) INFORMATION FOR SEQ ID NO:4:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:4:

UUGCCCACAU                                                                                                10

( 2 ) INFORMATION FOR SEQ ID NO:5:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:5:

UUGCUCACAC                                                                                                10

( 2 ) INFORMATION FOR SEQ ID NO:6:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:6:

CUGCCCACAU                                                                                                10

( 2 ) INFORMATION FOR SEQ ID NO:7:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:7:

CUGUUUACAU                                                                                                10

( 2 ) INFORMATION FOR SEQ ID NO:8:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

AAGACGTCTT GCG                                                                                            13

( 2 ) INFORMATION FOR SEQ ID NO:9:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:9:

UGGUGGGCGC  10

( 2 ) INFORMATION FOR SEQ ID NO:10:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:10:

GGCAAGAGUG  10

( 2 ) INFORMATION FOR SEQ ID NO:11:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:11:

CGUCGGUGUG  10

( 2 ) INFORMATION FOR SEQ ID NO:12:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:12:

GUCGGUGUGG  10

( 2 ) INFORMATION FOR SEQ ID NO:13:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

GATCTATGGT  10

( 2 ) INFORMATION FOR SEQ ID NO:14:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GTGATCTATG  10

( 2 ) INFORMATION FOR SEQ ID NO:15:

( i ) SEQUENCE CHARACTERISTICS:
  ( A ) LENGTH: 10 base pairs
  ( B ) TYPE: nucleic acid
  ( C ) STRANDEDNESS: single
  ( D ) TOPOLOGY: linear ( i i ) MOLECULE TYPE: RNA ( x i ) SEQUENCE DESCRIPTION: SEQ ID NO:15:

GCGCCCACCA        10

( 2 ) INFORMATION FOR SEQ ID NO:16:

( i ) SEQUENCE CHARACTERISTICS:
  ( A ) LENGTH: 10 base pairs
  ( B ) TYPE: nucleic acid
  ( C ) STRANDEDNESS: single
  ( D ) TOPOLOGY: linear ( i i ) MOLECULE TYPE: RNA ( x i ) SEQUENCE DESCRIPTION: SEQ ID NO:16:

CACUCUUGCC        10

( 2 ) INFORMATION FOR SEQ ID NO:17:

( i ) SEQUENCE CHARACTERISTICS:
  ( A ) LENGTH: 10 base pairs
  ( B ) TYPE: nucleic acid
  ( C ) STRANDEDNESS: single
  ( D ) TOPOLOGY: linear ( i i ) MOLECULE TYPE: RNA ( x i ) SEQUENCE DESCRIPTION: SEQ ID NO:17:

CACACCGACG        10

( 2 ) INFORMATION FOR SEQ ID NO:18:

( i ) SEQUENCE CHARACTERISTICS:
  ( A ) LENGTH: 10 base pairs
  ( B ) TYPE: nucleic acid
  ( C ) STRANDEDNESS: single
  ( D ) TOPOLOGY: linear ( i i ) MOLECULE TYPE: RNA ( x i ) SEQUENCE DESCRIPTION: SEQ ID NO:18:

CCACACCGAC        10

DETERMINATION OF OLIGONUCLEOTIDES FOR THERAPEUTICS, DIAGNOSTICS AND RESEARCH REAGENTS

CROSS REFERENCE TO RELATED APPLICATIONS

This application is a continuation-in-part of PCT/US92/07489 filed Sep. 4, 1992 which is a continuation-in-part of U.S. Ser. No. 755,485 filed Sep. 5, 1991 now abandoned and entitled "Determination of Oligonucleotides for Therapeutics, Diagnostics and Research Reagents" both of which are assigned to the assignee of the present application and incorporated by reference herein in their entirety.

FIELD OF THE INVENTION

This invention relates to in vitro selection of oligonucleotide sequences which selectively bind to a target biomolecule under physiological conditions. In accordance with preferred embodiments, therapeutic oligonucleotides are identified.

BACKGROUND OF THE INVENTION

The development of new drugs and biologically active substances for therapeutic, diagnostic and research reagent purposes traditionally concentrates on the rational design of such compositions based upon knowledge of the target biomolecule, i.e. the molecule to be modulated.

Bodily states in mammals, including many disease states, are effected by biomolecules. Classical therapeutics has generally focused upon interactions with proteins in efforts to modulate disease-potentiating functions of such proteins. In addition to modulating disease-potentiating functions of proteins directly, recent attempts have been made to moderate the actual production of proteins by interactions with molecules that direct their synthesis, intracellular RNA. Biological functions may also be modulated or regulated by interactions with other biomolecules such as nucleic acids, carbohydrates, lipids, steroids or toxins.

One approach for constructing therapeutics, diagnostics and research reagents has been simple modifications of known amino acid or nucleic acid sequences. Such techniques are limiting because the number of individual sequences of simple modifications necessary for the development of new substances is prohibitively large. In addition, many drug targets and other target molecules are too extensive and complex to be analyzed by these mutational experiments. Other biomolecule targets, by virtue of their particular chemical nature, are not candidates for directed mutagenesis of this sort. Some examples of such biomolecules are carbohydrates, lipids, and steroids.

Recently, methods have been devised whereby therapeutics, diagnostics and research reagents can be developed more quickly. A variety of combinatorial strategies have been described to identify active peptides. Houghton, et al. *Nature*1991, 354, 84; Lam, et al., *Nature* 1991, 354, 82; Owens, et al., *Biochem. Biophys. Res. Commun.* 1991, 181, 402; Fodor, et al., *Science*1991, 251, 767; Geysen, et al., *Molecular Immunology*1986, 23, 709; Zuckermann, et al., *Proc. Natl. Acad. Sci.* 1992, 89, 4505; Rutter, et al., U.S. Pat. No. 5,010,175 issued Apr. 23, 1991; Lam, et al., PCT US91/06444 filed Jul. 1, 1991, Dooley, et al., *Proc. Natl. Acad. Sci. U.S.A.*, 1993, 90, 10811; Dooley and Houghten, *Life Sciences*, 1993, 52, 1509; Ohlmeyer, et al., *Proc. Natl. Acad. Sci.* U.S.A., 1993, 90, 10922; Jayawickreme, et al., *Proc. Natl. Acad. Sci.* U.S.A., 1994, 91, 1614.

Rutter, et al. describes a method whereby statistically randomized peptides may be prepared and active peptide selected for and identified.

Lam, et al., teaches the preparation of randomer libraries, especially random peptide libraries in which each randomer sequence is individually coupled to a solid support (i.e. one oligomer sequence/one bead). Further, a reporter group is attached to each oligomer/bead in order to identify active oligomers from inactive oligomers. The randomer libraries of Lam, et al., PCT US91/04666 filed Jul. 1, 1991, are contacted with a target biomolecule and active randomers, identified via reporter groups, are isolated using the solid support to manually remove the active randomer from the rest of the library. Lam, et al. further teaches that the selected randomer can be characterized such as by Edman degradation or FAB-MS.

Combinatorial strategies for nucleic acids have also been developed. Such methods generally select for a specific nucleic acid sequence from a pool of random nucleic acid sequences based on the ability of the selected sequence to bind to a target protein. The selected sequences are then commonly amplified and the selection process repeated until a few strongly binding sequences are identified. Commonly, the pool of random nucleic acid sequences is comprised of short random sequences embedded in external flanking or "carrier" nucleic acid molecules of known sequence. Such carrier molecules are intended to neither enhance, nor detract from binding of the oligonucleotide. The amplification primers are prepared to be complementary to known sequences of the "carrier" generally of lengths 20 nucleotides in length or more. Such "carrier" portions are meant to facilitate manipulation of the molecule and preferably have neutral effect upon the randomized sequence to be selected for. Using this method Tuerk and Gold, *Science*1990, 249,505; identified a sequence which strongly binds T4 polymerase binding protein, gp43, but which would not have been predictable using traditional methods. Ellington and Szostak, *Nature*1990, 346, 818; identified sequences which bind small ligands using this method, Bock, et al., *Nature* 1992, 355, 564; designed DNA molecules which recognize the protease thrombin and Schneider, et al., *J. Mol. Biol.*, 1992, 228, 862; isolated RNA ligands with high affinity for the bacteriophage R17 coat protein. More recently, using this method, Schneider, et al., *FASEB J.*, 1993, 7, 201; identified RNA molecules from a pool of RNA molecules that bind tightly to the *E. coli* transcription termination factor rho and Jellinek, et al., *Proc. Natl. Acad. Sci. U.S.A.*, 1993, 90, 11227; isolated RNA ligands with low-nanomolar affinity and high specificity to basic fibroblast growth factor from a library of RNA molecules.

Randomer oligonucleotide libraries are also mentioned by Lam, et al. Characterization of selected oligonucleotides after manual separation is suggested using the techniques of Maxam and Gilbert or by the use of an oligonucleotide sequencer. Electrospray-high performance mass spectrometry is also suggested in order to determine sequences and structures of randomers. These methods require the addition of a reporter group to the oligomer species in order to identify and manually isolate active oligomers. Furthermore, randomer libraries are limited to oligomers approximately 5mers in length since preparation of more than 5mers would present unwieldy amounts of oligomer/beads as well as the need for large amounts of target.

While some advantages have been achieved by the foregoing methods, simple methods of determining therapeutics, diagnostics, and research reagents are desirable. Previous methods have relied upon complex nucleic acid molecules comprised of at least partially random sequence portions to be selected for, as well as lengthy flanking carrier portions necessary to support the reactions. Still other methods are limited in the length of oligonucleotides within the randomer library which is physically possible. Methods requiring enzymatic amplification of active sequences are often limited by incompatibility with many non-standard nucleotides or nucleosides.

Methods in which selection may be carried out with a fully sequence-randomized pool of discrete molecules and a minimum of other fixed sequences would be greatly desirable as they would increase specificity, facilitate manipulation of the pool of molecules, and eliminate any indeterminate bias in binding selection resulting from the presence of either internal sequence fixed (unrandomized) positions and/ or the carrier portions.

Such improved methods to determine oligonucleotides for antisense therapeutics, diagnostics and research reagents are greatly desired.

Although oligonucleotides are currently being administered as therapeutic agents, it is not known a priori how to select an ideal nucleotide sequence to bind selectively to a target molecule. Moreover, in many cases, it is even difficult to decide what region of a gene or protein, for example, to target in order to achieve maximum effect. The methods of the present invention overcome these difficulties.

SUMMARY OF THE INVENTION

In accordance with some embodiments of the present invention, methods of determining oligonucleotides that target the sequence and/or structure of a target biomolecule and have specific activity for that target biomolecule are provided. In accordance with said methods a set of randomized oligonucleotides may be prepared and assayed for activity against the target biomolecule. Active and inactive oligonucleotides are separated by microanalytical techniques and the active oligonucleotides are characterized by microanalytical structure determination. In other embodiments of the present invention, oligonucleotides having specific activity for a target biomolecule are determined by preparing a set of randomized oligonucleotides and assaying the set of random oligonucleotides for activity against a target biomolecule. Active and inactive oligonucleotides are separated and active oligonucleotides are recovered. Thereafter active oligonucleotides are amplified by extending a polyA sequence in a 3' direction on the active oligonucleotide. A first chimeric primer comprising a 5' known sequence and a 3' polydT portion may be hybridized to the oligonucleotide and a cDNA strand may be prepared which is complementary to the oligonucleotide using the first chimeric primer. The cDNA may be extended in a 3' direction by the addition of polyA. Thereafter, the oligonucleotide and cDNA strands are separated and a second chimeric primer having a 5' known sequence and a 3' polydT portion is hybridized to the polyA portion of the cDNA resulting in the formation of recessed 3' ends on both strands. The recessed ends may be filled to form two complementary strands and the strands separated and amplified using polymerase chain reaction. The first and second chimeric primers may serve as PCR primers in some embodiments of the present invention. Furthermore, the oligonucleotide starting product, having been amplified, may be excised from the total PCR product and may be recovered and used in subsequent assay and amplification steps in order to optimize determination of oligonucleotides specifically active for a given target biomolecule.

In accordance with other methods of the present invention methods of determining oligonucleotides having specific activity for a target biomolecule are provided comprising the steps of preparing a set of randomized oligonucleotides and assaying the set of randomized oligonucleotides for activity against a target biomolecule. Active oligonucleotides are separated from inactive oligonucleotides and recovered. Recovered oligonucleotides are characterized to provide an oligonucleotide cassette. Thereafter a set of oligonucleotides comprising an oligonucleotide cassette and at least one flanking region of randomized positions are prepared and assayed for activity against a target biomolecule. Active oligonucleotide are separated from inactive oligonucleotides and active oligonucleotides are recovered. Thereafter the recovered oligonucleotides are characterized to provide a new oligonucleotide cassette. This new oligonucleotide cassette may be used in subsequent preparation, assay and characterization steps in order to optimize determination of oligonucleotides specifically active for a given target biomolecule.

In yet further embodiments of the present invention sets of sequence position randomized oligonucleotides may be subfractionated and assayed for activity for a target biomolecule. Oligonucleotides from the subfraction having the highest activity for a biomolecule may then be assayed, separated from inactive oligonucleotides and characterized in accordance with methods of the invention.

In other embodiments of the present invention methods of amplifying oligonucleotides are provided. PolyA may be extended in a 3' direction on the oligonucleotide to be amplified. A first chimeric primer comprising a 5' known sequence and a 3' polydT portion may be hybridized to the oligonucleotide and a cDNA strand may be prepared which is complementary to the oligonucleotide using the first chimeric primer as a primer. The cDNA may be extended in a 3' direction by the addition of polyA. Thereafter, the oligonucleotide and cDNA strands are separated and a second chimeric primer having a 5' known sequence and a 3' polydT portion is hybridized to the polyA portion of the cDNA resulting in the formation of recessed 3' ends on both strands. The recessed ends may be filled to form two complementary strands and the strands separated and amplified using polymerase chain reaction. The first and second chimeric primers may serve as PCR primers in some embodiments of the present invention.

In accordance with other embodiments of the present invention, a set of randomized oligonucleotides are prepared and allowed to bind to the target nucleic acid. The active oligonucleotides are identified and sequenced by mapping the target site to which the oligonucleotides have bound, and this is accomplished by affinity cleavage using enzymatic or chemical cleavage.

In yet other embodiments, affinity mapping may be followed by a footprinting assay aimed at optimizing the sequence and length of oligonucleotides for enhanced binding to the preferred target site.

In accordance with still other embodiments of the present invention, oligonucleotides identified in accordance with methods of the present invention may be employed further in diagnostic and research methods for the detection of chemicals or drugs present in a sample.

Oligonucleotides identified in accordance with the methods of the present invention are also encompassed by the present invention. Oligonucleotides identified and sequenced in accordance with methods of the present invention are likewise encompassed by the present invention. In accordance with other embodiments of the present invention diagnostic and research reagents are provided.

DETAILED DESCRIPTION OF PREFERRED EMBODIMENTS

Methods of determining oligonucleotides that are specifically active against target biomolecules are provided. In the context of the present invention "determine" refers to the identification of the sequence of oligonucleotides and the binding activity of the oligonucleotides for a target molecule. Further, "determine" refers to the identification of oligonucleotides having activity such as catalytic or enzymatic activity. In some instances, neither the oligonucleotide sequence nor its specific activity is known prior to performance of methods of the present invention. In other cases, while a particular oligonucleotide sequence may be known, those skilled in the art may not recognize its activity for a particular target molecule. In still other cases, activity of a known sequence for a particular target molecule may be optimized.

In some embodiments of the present invention, "specific activity" refers to binding affinity of said oligonucleotides for a target molecule, and further encompasses activity such as catalytic or enzymatic activity. As used herein, binding affinity refers to the ability of the oligomer to bind to a target molecule via hydrogen bonds, van der Waals interactions, hydrophobic interactions, or otherwise. For example, an oligonucleotide may have binding affinity for another oligonucleotide to which it is complementary, i.e., to which it has the ability to hybridize due to Watson-Crick base pair attraction. Thus active oligonucleotides have specific activity, be it binding, catalytic, enzymatic, or other activity for a target molecule, while inactive oligonucleotides exhibit minimal or no specific activity for a target biomolecule. The amount of activity sufficient to differentiate an active oligonucleotide from an inactive oligonucleotide will, of course, vary depending upon the parameters of the assay and the biomolecule targeted.

In accordance with said methods randomized oligonucleotides are prepared. In the context of this invention, the term "oligonucleotide" refers to a polynucleotide formed from naturally occurring bases and furanosyl groups joined by native phosphodiester bonds. This term effectively refers to naturally occurring species or synthetic species formed from naturally occurring subunits or their close homologs. The term "oligonucleotide" may also refer to moieties which have portions similar to naturally occurring oligonucleotides but which have non-naturally occurring portions. Thus, oligonucleotides may have altered sugar moieties or intersugar linkages. Exemplary among these are the phosphorothioate and other sulfur-containing species which are known for use in the art. In accordance with some preferred embodiments, at least some of the phosphodiester bonds of the oligonucleotide have been substituted with a structure which functions to enhance the stability of the oligonucleotide or the ability of the oligonucleotide to penetrate into the region of cells where the viral RNA is located. It is preferred that such substitutions comprise phosphorothioate bonds, phosphotriesters, methyl phosphonate bonds, short chain alkyl or cycloalkyl structures or short chain heteroatomic or heterocyclic structures. Most preferred are $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ structures. Also preferred are morpholino structures. Summerton, J. E. and Weller, D. D., U.S. Pat. No. 5,034,506 issued Jul. 23, 1991. In other preferred embodiments, such as the protein-nucleic acid (PNA) backbone, the phosphodiester backbone of the oligonucleotide may be replaced with a polyamide backbone, the bases being bound directly or indirectly to aza nitrogen atoms within the polyamide backbone. P. E. Nielsen, et al., Science 1991 254 1497. In accordance with other preferred embodiments, the phosphodiester bonds are substituted with other structures which are, at once, substantially non-ionic and non-chiral, or with structures which are chiral and enantiomerically specific. Persons of ordinary skill in the art will be able to select other linkages for use in practice of the invention.

Oligonucleotides may also include species which include at least some modified base forms. Thus, purines and pyrimidines other than those normally found in nature may be so employed. Similarly, modifications on the furanosyl portion of the nucleotide subunits may also be effected, as long as the essential tenets of this invention are adhered to. Examples of such modifications are 2'-O-alkyl and 2'-halogen-substituted nucleotides. Some specific examples of modifications at the 2' position of sugar moieties which are useful in the present invention are OH, SH, $SCH_3$, F, OCN, $O(CH_2)_nNH_2$, $O(CH_2)_nCH_3$ where n is from 1 to about 10; $C_1$ to $C_{10}$ lower alkyl, substituted lower alkyl, alkaryl or aralkyl; Cl, Br, CN, $CF_3$, $OCF_3$, O—, S—, or N-alkyl; O—, S—, or N-alkenyl; $SOCH_3$, $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. Sugar mimetics such as cyclobutyls may also be used in place of the pentofuranosyl group. Nucleotides may also comprise other modifications consistent with the spirit of this invention. Such nucleotides are best described as being functionally interchangeable with, yet structurally distinct from, natural nucleotides. All such nucleotides are comprehended by this invention so long as they effectively function as subunits in the oligonucleotide.

In some embodiments of the present invention oligonucleotide groups may be detectably labeled. Reporter groups can be incorporated as polymerizable monomer units such as phosphoramidites, usually at the 3' or 5' ends of the oligonucleotides. Labelling may also be performed following completion of combinatorial library synthesis such as by chemical modification such as post-synthesis conjugation. Radiolabels such as $^3H$, $^{14}C$, $^{35}S$, $^{32}P$, $^{33}P$ and $^{18}O$ may be incorporated by methods known to those skilled in the art. For example, oligonucleotides may be labeled at their 5' termini using [$\gamma$-$^{32}P$] ATP and T4 polynucleotide kinase. Furthermore, fluorescent, chemoluminescent, spinlabel, and redox reactive (i.e. for electrochemical detection) groups are commonly employed by those skilled in the art. One skilled in the art would recognize that differential bias caused by the incorporation of such a label should be avoided. Thus, in some embodiments of the present invention each individual sequence member of the combinatorial pool is labeled identically. It should be further recognized that the reporter group may contribute to the specific activity of an oligonucleotide. Thus, the reporter group may be treated as another monomer unit analog and permanently incorporated into the composition.

Unlabeled oligonucleotides determined according to the present methods may be sequenced, and this sequence information may be used to resynthesize labeled oligonucleotides. Labeled oligonucleotides may be useful as probes or in other assays by virtue of their specific activity for a target molecule and their ease of detection.

Oligonucleotides of the present invention may be of predetermined length. It is preferred that such oligomers be from about 6 to about 50 units in length. It is more preferred that such oligomers be from about 10 to about 20 units in length.

In some aspects of the present invention oligonucleotides may be in solution. In other aspects of the invention sequence randomized oligonucleotides may be bound to solid support without sequence preference.

Optimization of Sequence Determination: The term "random", as used herein, is used in the sense of oligonucleotides having truly random base sequence, formed through solid state synthesis. This method need not, however, be completely and statistically random in fact. Thus, enrichment of oligonucleotides in certain bases may be desired in accordance with some embodiments of this invention. In the context of the present invention a random oligonucleotide pool or library is a set of oligonucleotides having sequences representing every possible combination of nucleotide units within the randomized positions. Thus, in accordance with the present invention an oligonucleotide may have a complexity of $P^N$ where P is the number of different units used and N is the number of positions in an oligonucleotide which are randomized. For example, an oligonucleotide pool of oligonucleotides having six random positions comprising four different subunits would have a complexity of $4^6$ or 4096 different sequences representing every possible combination of subunits. Of course, a randomer pool may not necessarily be random in fact, and enrichment of oligonucleotides in certain bases may be desired in accordance with some embodiments of this invention.

Unlike the preparation of randomized peptide libraries which have large degrees of incorporation bias away from the molar ratio of the premixed unit members, Rutter and Santi, U.S. Pat. No. 5,010,175 issued Apr. 23, 1991, the coupling efficiencies of natural nucleotide units and of analogs of limited chemical diversity using commercially available automated synthesizers and standard phosphoramidite chemistry known to those skilled in the art appears to be very similar. That is, near equimolar incorporation at a given randomized position of all monomer unit members of an equimolar mixture is obtained for randomized libraries of sufficient total quantity and limited complexity. Thus, in accordance with preferred embodiments of the present invention, columns of a DNA synthesizer may be packed with a mixture containing an equal amount of adenosine(A)-, cytidine(C)-, guanosine(G)- and uracil(U) (or thymidine (T))-controlled pore glass (CPG, Chemgenes, Needham, Mass.). At each "random" coupling step, an equimolar mixture of all four phosphoramidites may be delivered to each column. Nucleic acid synthesizers are commercially available and their use is generally understood by persons of ordinary skill in the art to generate nearly any oligonucleotide of reasonable length which may be desired. In some preferred embodiments of the present invention the sequence randomized oligonucleotides are cleaved from the controlled pore glass to provide a pool of sequence randomized oligonucleotides in solution.

Randomized oligonucleotides made using monomer groups having greater sequence and structure complexity may require appropriate premixture ratio correction factors in order to obtain equimolar incorporation of any monomer unit in the presence of any other monomer units at randomized sequence positions of combinatorial libraries of the present invention. Strategies to determine coupling efficiencies and to correct for any observed coupling bias are known to those skilled in the art. For example, Rutter and Santi, U.S. Pat. No. 5,010,175 issued Apr. 23, 1991 and Lam, et al., PCT US91/06444 filed Jul. 1, 1991, describe strategies to accommodate incorporation bias in randomer peptide libraries.

There is a complexity limit to the detectability of specific activity (signal to noise), especially in longer oligonucleotide libraries composed of larger numbers of chemically distinct monomer units in which the oligonucleotides have a high percentage of randomized positions. It is likely that with short, i.e. 8–10 nucleotides in length, unstructured, conformationally dynamic oligonucleotides, such as might commonly be used to initially limit complexity to facilitate identification of highest specific activity sequences, a plethora of relatively weak specific activity towards many target molecules will result. Procedures useful for increasing the complexity of an oligonucleotide pool and for increasing the specific activity of oligonucleotide pool are encompassed by the present invention.

The use of additional units such as nucleotide analogs may be preferred in some instances where it is desirable to increase the complexity of the group of oligonucleotides, thereby increasing the specific activity. The complexity of a group of random oligonucleotides is represented by the formula $P^N$ where P is the number of different units used and N is the number of positions in an oligonucleotide which are randomized. Table 1 illustrates the change in group complexity as a result of the increase in the number of analogs used.

TABLE I

Oligonucleotide: NNNNNN

| Number of different analogs used (P) | Complexity of each set (Q) ($P^6$) |
|---|---|
| 4 | $4^6 = 4096$ |
| 5 | $5^6 = 15,625$ |
| 6 | $6^6 = 46,656$ |
| 7 | $7^6 = 117,649$ |
| 8 | $8^6 = 262,144$ |
| 9 | $9^6 = 531,441$ |
| 10 | $10^6 = 1,000,000$ |

Initial screening protocols may be useful to determine whether a given monomer unit or analog will have a positive, negative or neutral effect in a given library pool for a pre-chosen target. Determination can be made by incorporating equimolar amounts of all chosen monomer units at every position of a pool and comparing the specific activity of the pool for a target molecule to the specific activity of a combinatorial pool prepared without the monomer unit in question.

An additional method of increasing the specific activity of a group of oligonucleotides is to constrain the oligonucleotide conformationally in order to provide the correct presentation of the randomer oligonucleotide for the target biomolecule. There are two general classes of conformationally constrained chemistries, noncovalent and covalent. Noncovalent bonding is generally easier as it can be achieved without additional chemistry steps. For example, an oligonucleotide may be conformationally constrained by providing short complementary ends at the 3' and 5' termini of the region of interest, which region of interest comprises randomized positions. Generally the complementary ends range in length from about 3 to about 8 nucleotides in length. The complementary ends will hybridize to form secondary structure thereby providing correct presentation of the randomized portion of the oligonucleotide to the target biomolecule. In accordance with other aspects of the invention, noncovalent conformational constraints may be achieved with physiologic divalent metal bridge chelation of the 5' and 3' ends of oligonucleotides.

Covalent constraints may also be provided by the incorporation of complementary reactive groups at different fixed positions in the oligonucleotides of the combinatorial library. This may result in spontaneous unique covalent bond formation to form crosslinks, under the appropriate reaction conditions which will be apparent to those skilled in the art. Reactive groups and nucleotide analogs useful in the formation of crosslinking groups are described for example, by U.S. Ser. No. 846,376 filed Mar. 5, 1992 and incorporated by reference herein in its entirety.

Detectable specific activity may also be enhanced by a sequential method in which evolutions of oligonucleotide pools, each of greater complexity than its predecessors, are assayed for specific activity and characterized. This method allows selection in a randomized environment within a complexity limit that is easily handled. Thus, for example, during one round of determination performed in accordance with methods of the present invention an oligonucleotide specific for a target biomolecule is identified from a random pool of oligonucleotides. Thereafter, a next pool of longer oligonucleotides may be prepared capitalizing upon the oligonucleotide sequence determined in the previous step (i.e. a cassette) by incorporation of the determined sequence or cassette into the sequence of the pool to provide a pool of oligonucleotides having at least one cassette and at least one flanking region of randomized positions. Thereafter the pool of oligonucleotides is assayed for specific activity for a target biomolecule, and the sequence of the active oligonucleotide or oligonucleotides is determined. This procedure may be performed iteratively, building the oligonucleotides of each new round based upon the determined sequences from the previous step or steps.

In some embodiments of the present invention it may also be desirable to subfractionate a pool of sequence randomized oligonucleotides to provide subfractions of the oligonucleotide pool, thus limiting the degree of complexity of each subfraction that is assayed at one time. This both diminishes the amount of total material that must be used in a determination in order to have sufficient representation of all individual sequences and it also enhances the signal to noise ratio of the assay by starting with an oligonucleotide subfraction enriched in the most active sequences. Any physical-chemical or functional characteristic, combined with an appropriate separation modality may be used to empirically subfractionate a group, thereby resulting in (or deriving) numerous distinct subfractions of diverse character, and diminished complexity. It is theorized that if a sequence (or sequences) exists within the original group that have high affinity and specificity for a particular target, it will be found enriched in a limited number of the reduced complexity subfractions.

One skilled in the art would be apprised of the broad selection of appropriate selection modalities which are available. The strategy followed will of course depend upon the properties of the elements of the oligonucleotide pool. It will further be appreciated by one skilled in the art that as the number of group elements increases and the structural and chemical diversity enlarges, there will be a greater selection of separation strategies leading to increased subfractionation capacity. By way of example, it is envisioned that novel oligomers may be resolved into subfractions by any one or a combination of size, positive or negative charge, hydrophobicity and affinity interactions. Many chromatographic and analytical instrumental methods are known to those skilled in the art which may be effectively applied to the separation strategies encompassed herein.

Targets: Target molecules of the present invention may include any of a variety of biologically significant molecules. By biologically significant, one skilled in the art would understand that molecules inherently related to some biological function are intended. In addition, biological significance need not be limited to disease related significance, but may also mean significance to, for example, the greater understanding of biological functions, or the greater ability to monitor or control normal biological function. Target molecules may be nucleic acid strands such as regions of DNA or RNA. Target molecules may also be proteins, glycoproteins, carbohydrates, lipids, toxins, steroids, drugs or cofactors. In some preferred embodiments of the present invention, said target molecule is a protein such as an immunoglobulin, receptor, receptor binding ligand, antigen or enzyme and more specifically may be a phospholipase, tumor necrosis factor, endotoxin, interleukin, plasminogen activator, protein kinase, cell adhesion molecule, lipoxygenase, hydrolase or transacylase. In other preferred embodiments of the present invention said target molecules may be important regions of DNA or RNA of the human immunodeficiency virus, Candida, herpes viruses, papillomaviruses, cytomegalovirus, rhinoviruses, hepatitis viruses, or influenza viruses. In still further preferred embodiments of the present invention said target molecule is ras 47-mer stem loop RNA, the TAR element of human immunodeficiency virus, the gag-pol stem loop of human immunodeficiency virus (HIV), the RRE element of HIV, the HIV tat protein or the 5'-UTR of Hepatitis C virus. Still other targets may induce cellular activity. For example, a target may induce interferon.

In some aspects of the present invention, a target protein may be identified based upon the fact that proteins bind to free aldehyde groups while nucleic acids do not. Thus, a sampling of proteins which have been identified as potential targets may be bound to solid supports having free aldehyde groups such as nitrocellulose filters. For example, up to 96 proteins may be bound in individual wells of a 96-well nitrocellulose filter manifold. In some embodiments of the present invention sequential concentrations of protein may be tested to determine the effect of lowering the protein target concentration. Thereafter, an identical detectably labeled oligonucleotide group may be incubated with each protein sample under binding conditions. The preparation of labeled oligonucleotide groups is described herein. The support is washed and the presence or absence of binding is detected whereby binding indicates that the oligonucleotide group has specific activity for a given protein. As will be apparent to one skilled in the art, methods of detection of binding will be dependent upon the label used.

Detection: Specific activity of oligonucleotides of the present invention may be detected by methods known to those skilled in the art. At least a portion of the random oligonucleotide pool will most preferably have specific activity for a target molecule. The remaining oligonucleotides may be separated from the active oligonucleotides by methods such as are disclosed herein. Appropriate assays will be apparent to one skilled in the art and oligomer concentration, target molecule concentration, salt concentration, temperature, buffer and buffer concentration may be altered to optimize a particular system. Initial assay conditions should preferably be compatible with further steps in the procedure. For example, high concentrations of salt or reagents which may interfere with binding should be avoided in some embodiments of the invention. In some preferred embodiments of the present invention, binding conditions simulate physiological conditions. In other preferred embodiments of the present invention binding occurs in a buffer of from about 80 mM to about 110 mM sodium chloride and from about 10 to about 15 mM magnesium chloride. Oligomers may also generally be assayed for catalytic or enzymatic activity.

Gel shift assays may be used to visualize binding of an oligomer to a target molecule and separate bound from unbound oligonucleotides. In accordance with methods of the present invention, radiolabelled target molecule bound to oligomer of the present invention may be run on a gel such as a polyacrylamide gel. Bound target molecule has less mobility than unbound target molecule, and therefore will not migrate as far on the gel. The radioactive label allows visualization of the "shift" in mobility by standard procedures for example, by means of autoradiography or by using a phosphorimager (Molecular Dynamics). In other embodiments of the present invention a gel shift assay may be performed wherein an unlabeled target molecule may be detected preferentially bound to radiolabeled oligonucleotide selected from the sequence randomized oligonucleotide pool.

Streptavidin-biotin capture is another useful assay for the detection of specific activity and separation of active oligonucleotide from inactive oligonucleotides. A target may be biotinylated prior to incubation with a radioactively labeled random oligonucleotide pool. Biotinylation of target is a well known procedure which may be accomplished through a number of known procedures. For example, an RNA target may be biotinylated using 5' kinase reactions. The oligonucleotide pool is thereafter incubated with the target and the target molecule is captured on streptavidin-coated solid support. Consequently any oligonucleotide which is bound to the target will also be captured. Any of a broad range of solid supports known in the art could effectively be used in methods of the invention. For example, streptavidin-coated solid supports are available commercially such as for example, streptavidin-coated magnetic beads available from Promega (Madison, Wis.) and streptavidin coated microtitre plates (Covalink) available from NUNC (Raskilde, Denmark) or Labsystems (Marlboro, Mass.). The solid support may be washed and the reaction may be reequilibrated to further enrich the "winning" sequence.

Affinity mapping by enzymatic or chemical cleavage may be used to detect binding site(s) for an oligonucleotide to a target molecule or preferred binding site(s) for members of a pool of oligonucleotides, and determine the sequence of the hybridization site(s) on said target molecule. This may be achieved by using chemical (e.g. permanganate) or enzymatic (single-strand specific RNases, e.g. RNase H, RNase CL3, RNase T1) cleavage. In accordance with methods of the present invention, target RNA to which members of a random pool of oligodeoxyribonucleotides are bound is subjected to cleavage mapping by contacting with the cleaving agent. Only target bound to oligonucleotide will result in cleavage of the target at the site of heteroduplex formation. As a result, the preferred hybridization site on the target RNA can be identified and its sequence determined.

Assays are not limited to detecting binding affinity but may also detect other desired activities such as biological responses such as catalytic or enzymatic activity. It should be recognized that functional activities are always mediated by prior binding interactions. Thus, selection for function is also selection for binding.

Positive functional selection is preferred in some embodiments of the present invention. For example, selection for catalytic function may be achieved by covalently coupling the moiety containing a scissile bond to be bound and cleaved to a solid support with a noncleavable linker. The other side of the moiety containing the said cleavable bond is coupled to one end of oligonucleotides of the combinatorial pool. The pool is thus covalently coupled to the solid support via the intermediate substrate containing the bond to be cleaved. Only those sequences in the pool capable of binding to the substrate and cleaving the only reactive bond present will release themselves from covalent capture on the solid support. These sequences may then be recovered from the solution phase and characterized. In the alternative, only those sequences that catalyze bond formation will bind covalently to the solid support via a reversible linker. The non-bound oligonucleotides may be washed away and the reversible linker cleaved to release the active sequences. Solid supports, noncleavable and reversible linkers and attendant conjugation chemistry are well known in the art.

Separation: Techniques such as continuous flow mass transport methodologies (Giddings, J. Calvin, *Unified Separation Science*, John Wiley and Sons, Inc., New York, 1991) may be also performed to identify active oligonucleotides and separate active from inactive oligonucleotides. Any of a broad range of methodologies which involve the use of continuous, differential mass transport flow via multiple competing equilibria between interacting species in a system with sufficient resolving power are envisioned for use in effecting desired resolution. Such methodologies must preserve and take advantage selectively of $k_d$ for the tightest complexes being the slowest of all competing on and off rate constants. Furthermore, selected methodologies must achieve high stringency separation while enhancing enrichment of bound complexes. Optimally the amount of target molecule should be much greater than the amount of individual sequences, but should not be greater than the amount of the total number of oligonucleotide sequences in the combinatorial library used. This formula will allow some limited competition of all individual sequences for binding to the target, yet there will be sufficient target to retain most of the preferred oligonucleotide. What will allow success is the provision of enough resolving capacity and power to handle the relative and absolute concentrations and mass amounts of all components and the differential affinity of their interactions according to the performance characteristics of the particular systems. (Giddings, *Unified Separation Science*, John Wiley and Sons, Inc., New York, 1991). Separation methodologies dependent on nonspecific physical-chemical properties may be employed. Preferred methodologies include those methodologies in which specific affinity interactions are utilized such as solid support based affinity chromatography wherein the target molecule is stably attached to a solid support and the ligands are in the flowing mobile phase. High specificity affinity separation can also be achieved when both the target molecule and the ligand pool are in the mobile phase. Forces effecting differential transport of bound target and free ligands is all that is required. Resolution may also be enhanced by the inclusion of a mass excess (over the randomized oligonucleotide ligand pool) of a uniformly nonspecific, weak binding molecule (such as bovine serum albumin) of the ligand pool that does not interact with the target molecule.

Representative resolution modalities which may be useful in methods of the present invention include, but are not limited to, size exclusion/gel filtration chromatography (Sephadex-LPLC or Superous-FPLC), isoelectric focusing (IEF) including Rotofor IEF (Bio-Rad), fast affinity chromatography (Beckman), electrophoresis methods, sedimentation methods, field flow fractionation (FFF), ion exchange chromatography, weak affinity chromatography; Zopf and Ohlson, *Nature*, 1990, 346, 87; affinity filtration, centrifugal countercurrent chromatography (CCC), perfusion chromatography, affinity chromatography on solid supports, and hydrophilic interaction chromatography.

Microanalytical resolution techniques may also be employed to separate active from inactive oligonucleotides. In some embodiments of the present invention microanalytical separation techniques may also be useful to resolve a group of active oligonucleotides. Microanalytical resolution technologies are well known in the art and any of the technologies will be useful in the present invention. For example, gas chromatography (gc), high performance liquid chromatography (HPLC), high performance capillary electrophoresis (HPEC), and field flow fractionation (FFF), (Giddings, J. Calvin, *Unified Separation Science*, John Wiley and Sons, Inc., New York, 1991), may be used alone or on-line with microanalytical characterization technologies. HPLC methods have evolved to accommodate the resolution of nanomole and lesser quantities of materials. For example, microbore HPLC on-line with mass spectrometry has been applied to resolve a combinatorial problem. Hunt, et al., *Science*, 1992, 255, 1261. HP capillary electrophoresis (HPCE) may also be effectively applied to resolve oligonucleotides. When HPCE is placed on-line with mass spectrometry there is no requirement to be able to directly resolve sequences prior to injection in the mass spectrometer. Use of this methodology is described in Toulas, et al., *LC-GC*, 1992, 10, 471 (detection of attomolar to zeptomolar amounts of fluorescence reporter group tagged oligonucleotides with laser-induced fluorescence detection); Rodrigues, et al., *Amer. Biotech. Lab.* 1992, 21, (capillary non-gel sieving electrophoresis of nucleic acids); Carchon, et al., *Amer. Biotech. Lab.* 1992, 67; Stevenson, *Amer. Lab*, 1992, 17; Stevenson, *Chem. and Engin. News*, 1992, 24, (miceliar electrokinetic capillary electrophoresis); Cobb, et al., *Anal. Chem.* 1992 (mapping and sequence determination of pre-fragmented oligomers from HPCE). Two dimensional electrophoresis of oligonucleotides may also be useful, especially where oligonucleotides are comprised of chemically diverse monomers.

In accordance with certain embodiments of the present invention active oligonucleotides are recovered. Recovery of active oligonucleotides, as used herein, refers to sufficient purification of the active oligonucleotide(s) for performance of subsequent steps. Thus, in some aspects of the invention that recovery of active oligonucleotides refers to separation of active oligonucleotides from target biomolecule. In some preferred embodiments of the present invention active oligonucleotides may be recovered attendant to separation of the active from inactive oligonucleotide. In other embodiments of the present invention, recovery requires additional steps. In still other embodiments of the present invention, only the binding of oligonucleotides to the target molecule may be determined, in which case recovery of the oligonucleotide may not be necessary.

Characterization: Active oligonucleotides may be characterized, such as by microanalytical characterization or standard nucleic acid sequencing. In some preferred embodiments of the present invention, separation, recovery, and characterization are accomplished by the use of microanalytical resolution technologies combined with microanalytical characterization technologies, performed individually or integrated such as in "on-line" systems for maximum efficiency and conservation of material.

The microanalytical technique mass spectrometry (MS) may be effectively used to characterize oligonucleotides. MS has been successfully applied to peptides. For example, Hunt, et al., *Science*, 1992, 255, 1261 and 1264 successfully identified the sequences of peptides (with theoretical complexity of $20^9$) selected for binding (intracellularly) to MHC receptor molecules. After recovery and crude purification away from contaminating cellular components, the preferred peptide-MHC complexes (>200) were dissociated and the peptides resolved by microcapillary HPLC on-line to electrospray ionization tandem quadrupole FAB-MS, which identified the sequences of eight of the peptides present in only sub-pmole amounts.

MS can also be applied to both fully and partially resolved oligonucleotides. Furthermore, new non-destructive volatilization procedures now allow for MS application to biopolymers and analogs. For example, electrospray ionization (Weinberger, *Amer. Lab.* 1992, 54; and laser desorption, (Romano and Levis, *J. Amer. Chem. Soc.*, 1991, 113, 9665.

In other preferred embodiments of the present invention oligonucleotides are characterized by amplification and sequencing. Thus, in accordance with the present invention, a polynucleotide tail such as polyA is added to the 3' end of the highest specific activity selected oligonucleotide(s) to form a first strand. The term polyA is used to refer herein to the addition of a riboadenosine (to tail an RNA molecule) or deoxyadenosine (to tail a DNA molecule) and may be added via terminal deoxynucleotidyl transferase (TdT) for DNA or polyrA polymerase for RNA. Other methods of providing polynucleotide tails known to those skilled in the art are also encompassed herein. A first chimeric primer is hybridized to the first strand. The first chimeric primer is comprised of a 5' known sequence and a 3' polynucleotide portion complementary to the polynucleotide tail of the first strand. Thus, in the present example the first chimeric primer is comprised of a known sequence and a 3' polydT portion. The 3' polynucleotide portion is preferably approximately from about 12 to about 16 nucleotides, and most preferably 15 nucleotides in length in order to optimize hybridization of the primer to the polynucleotide region of the first strand at lower temperatures. The 5' known sequence is preferably approximately 10 to about 15 nucleotides in length, and most preferably 12 nucleotides in length. The 5' known sequence is preferably also comprised of a high GC content that together with the 3' polynucleotide region allows for stringent binding at elevated temperatures. Thus, at higher temperatures required for PCR, there should be no cross-priming of the polynucleotide tails. In still further preferred embodiments of the present invention, the 5' region of the first chimeric primer may provide for one or more unique restriction sites. Such restriction sites may be useful for example, in forced cloning. Furthermore, the unique sequence serves a bookkeeping purpose in order to discriminate the sense from the antisense sequence in final sequencing. In yet further embodiments of the invention the first chimeric primer provides for mechanisms whereby the primer may be excised from the oligonucleotide of interest. For example, the first chimeric primer may incorporate a class IIS restriction endonuclease site. Class IIS restriction endonucleases ("shifters") cleave double stranded DNA at a precise number of nucleotides from the recognition site, regardless of the sequence of those nucleotides. For example, FokI cleaves double stranded DNA thirteen nucleotides from its recognition site, thereby removing the region downstream from the oligonucleotide of interest.

In still more preferred embodiments of the present invention a binding "handle" may be provided as a reactive group incorporated into the first chimeric primer. For example, a biotin moiety may be incorporated during synthesis at the 5' end of the first chimeric primer. Other binding "handles" will be apparent to one skilled in the art given the present disclosure.

In certain embodiments of the present invention, the first chimeric primer may be captured on a solid support. For example, the primer may be streptavidin captured using an incorporated biotin binding "handle". In other embodiments of the present invention the primer may be covalently attached to microtitre plates such as by modifications of the method described by Mitsuhashi, et al., *Nature*, 1992, 357, 519. Such capture may facilitate washing during the preparation of the flanking "primer sites" flanking either end of the oligonucleotide of interest.

Polymerase such as Taq I polymerase in the presence of an excess of all four nucleotides may be used to form cDNA complementary to the first strand using the first chimeric primer. The cDNA may be further extended at its 3' end with a polynucleotide tail such as polydA by addition of excess nucleotide in the presence of an appropriate enzyme such as TdT. For example, the cDNA may be further extended at its 3' end with a polydA by the addition of dATP in the presence of TdT. The first strand and the cDNA strand may subsequently be separated by heating.

A second chimeric primer may then be hybridized to the cDNA strand at a lower hybridization temperature, resulting in 3' recessed ends on both strands. The second chimeric primer, like the first, is comprised of a 5' known sequence and a 3' polynucleotide portion which is complementary to the polynucleotide tail of the cDNA. Thus, in the present example, the second chimeric primer has a 3' polydT portion which is complementary to the polyA tail of the cDNA. The 3' polynucleotide portion is preferably approximately from about 12 to about 16 nucleotides, and most preferably 15 nucleotides in length and the 5' known sequence is preferably approximately 10 to about 17 nucleotides in length, and most preferably 13 or 15 nucleotides in length. The 5' known sequence of the second chimeric primer is also comprised of a high GC content that together with the 3' polynucleotide region allows for stringent binding at elevated temperatures and may provide for a unique restriction site. The second chimeric primer also provides for mechanisms whereby the primer may be excised from the oligonucleotide of interest. For example, the second chimeric primer may incorporate a riboU at the 3' terminus. The ribophosphate diester bond may be cleaved by selective specific base (—OH) hydrolysis or RNase treatment, thus excising the primer and any upstream regions from the region downstream from the riboU site.

The recessed ends are filled in by the addition of a polymerase such as Taq I and an excess of all four nucleotides. Thus, using recessed ends as primers and the overhangs as templates, complementary strands are formed. The resulting fully complementary and fully duplex strands are separated by heating and polymerase chain reaction is performed to amplify the oligonucleotides. Polymerase chain reaction procedures are well known in the art. Ausubel, et al., *Current Protocols in Molecular Biology*, John Wiley and Sons, 1989. The first and second chimeric primers may effectively serve as PCR primers.

The amplified oligonucleotides may be force cloned using the primer sequence unique restriction sites or PCR product single base overhang cloned and sequenced by procedures known in the art. Alternatively, in some embodiments of the present invention the oligonucleotide of interest may be excised from the upstream and downstream flanking regions, re-assayed for selective binding, recovered and characterized. For example, by relying upon mechanisms incorporated within primers having the sequences GGATG $(dT)_{13}$ (SEQ ID NO: 1; first chimeric primer) and CGCTGG ATC CGC $(dT)_{14}rU$ (SEQ ID NO: 2; second chimeric primer) the oligonucleotide may be restricted with FokI, or the ribophosphate diester bonds may be selectively cleaved by hydrolysis or treatment with RNase to excise the original random oligonucleotide of interest from the flanking regions added herein to facilitate amplification of the oligonucleotides.

In other embodiments of the present invention, the sequence of an active oligonucleotide (one bound to a target molecule) may be determined by identifying the preferred binding site of the oligonucleotide to the target molecule. This can be followed by optimizing the binding of oligonucleotide to the target molecule. Oligonucleotides which optimally target the sequence and structure of a target biomolecule provide increased affinity and specificity, and thereby enhanced specific activity for that biomolecule. In one embodiment, methods of the present invention have been used to determine preferred hybridization sites on a target RNA molecule by means of affinity mapping using enzymatic or chemical cleavage techniques. Random oligonucleotide pools are mixed with the target molecule and allowed to hybridize. Stringent selection conditions are enlisted to drive the selection in favor of oligonucleotides that exhibited the highest affinity for the target RNA. This end is achieved by allowing hybridization to proceed under conditions wherein the concentrations of the individual oligonucleotides of the pool were much lower than the concentration of the target RNA. The location(s) of bound oligonucleotide(s) is then mapped using enzymatic or chemical cleavage. In one preferred embodiment, RNase H is used. RNase H is a ribonuclease that cleaves the RNA portion of a DNA:RNA hybrid, and thus, can be used to map the location of bound oligonucleotides on the target RNA. In a preferred embodiment, affinity mapping is followed by optimization of the oligonucleotide sequence and length for binding to these sites on the target RNA with a quantitative footprinting assay, which reveals the tightest binding oligonucleotides as indicated by the lowest $K_d$ values. This allows determination of those oligonucleotides that exhibit best binding to the preferred target site. A series of oligonucleotides are prepared which comprise a sequence complementary to at least a portion of the preferred target site identified by cleavage mapping. In a preferred embodiment, a set of oligonucleotides with overlapping sequences is prepared. The affinity of each oligonucleotide for the target is determined, and a $K_d$ for each is determined. The oligonucleotide with the lowest $K_d$ is the "winner," i.e. demonstrates optimal binding. $K_d$ can be determined by gel shift analyses or by footprinting. In a more preferred embodiment, "RNase ONE" is used for footprinting. "RNase ONE" is a base-independent, single strand-specific endoribonuclease. In other embodiments, single-strand specific RNases such as RNase T1, RNase CL3 or other enzymatic cleavers, or chemical cleaving agents such as permanganate are used. Oligonucleotides identified by this strategy have been shown to be functionally active inhibitors of target RNA expression.

The oligonucleotides of the present invention can be used in diagnostics, therapeutics and as research reagents. For therapeutic uses, an effective amount, ranging from 1 pg/kg to 1 g/kg of body weight, of the oligonucleotide is administered, to an animal, especially a human, suffering from a disorder effected by a biomolecule. Said biomolecule may be derived from an infectious agent such as a herpesvirus, or other viruses. Further, said biomolecule may be derived from a noninfectious agent of, for example, genetic origin. The regimen of administration may vary from once a day to several times a day, and may also be modified so as to administer the oligonucleotide several times a year or once in several years, depending on the degree of response observed. Effective amounts of therapeutic agents of the present invention, may be applied topically, intralesionally, orally, transdermally, intravenously or intramuscularly, as appropriate for the particular disorder to be treated. One skilled in the art would be apprised of the method most effective for any given disorder. Use of pharmacologically acceptable carriers is also preferred for some embodiments.

The oligonucleotides of the present invention may be used to detect and distinguish between two ligands, such as small, structurally closely-related molecules. For example, Jenison, et al., Science, 1994, 263, 1425, demonstrate the ability of RNA molecules to display a high degree of molecular recognition and discrimination between theophylline and caffeine. Their results demonstrate the utility of oligonucleotides as diagnostic agents. Oligonucleotides and methods of the present invention are also useful in research as they may be easily adapted to suit a range of assays. Oligonucleotides and methods of the present invention are also useful in therapeutics, for example, in processes such as pheresis, as highly specific sequestering agents for excess drug molecules, in the case of overdose. Thus, in accordance with methods of the present invention, oligonucleotides identified by methods of the present invention as being specific to a particular target molecule such as a drug or chemical, can be used to detect the chemical or drug in a sample such as a sample consisting of cells, tissues or bodily fluids, by contacting the sample contacting the sample with the oligonucleotide and detecting the presence or absence of binding by the oligonucleotide. The presence of binding is indicative of the presence of a specific chemical or drug in the sample. Binding assays are well known in the art. In preferred embodiments, the oligonucleotide is detectably labeled to facilitate detection of binding.

The following examples are illustrative, but not limiting of the present invention.

EXAMPLE 1

Synthesis of DNA Oligonucleotides

Unmodified DNA oligonucleotides were synthesized on an automated DNA synthesizer (Applied Biosystems model 380B) using standard phosphoramidite chemistry with oxidation by iodine. β-cyanoethyldiisopropyl phosphoramidites may be purchased from Applied Biosystems (Foster City, Calif.).

EXAMPLE 2

Synthesis of RNA Oligonucleotides

Unmodified RNA oligonucleotides having random base sequences were synthesized on an automated DNA synthesizer (Applied Biosystems model 380B) using modified standard phosphoramidite chemistry synthesis with oxidation by iodine. The standard synthesis was modified by increasing the wait step after the pulse delivery of tetrazole to 900 seconds. β-cyanoethyldiisopropyl phosphoramidites were purchased from Applied Biosystems (Foster City, Calif.). The bases were deprotected by incubation in methanolic ammonia overnight. Following base deprotection, the oligonucleotides were dried in vacuo. The t-butyldimethylsilyl protecting the 2' hydroxyl was removed by incubating the oligonucleotide in 1M tetrabutylammoniumfluoride in tetrahydrofuran overnight. The RNA oligonucleotides were further purified on $C_{18}$ Sep-Pak cartridges (Waters, Division of Millipore Corp., Milford, Mass.) and ethanol precipitated.

EXAMPLE 3

Synthesis of Phosphorothioate Oligonucleotides

Phosphorothioate oligonucleotides represent a class of oligonucleotide analog that is substantially nuclease resistant. Phosphorothioate RNA oligonucleotides and phosphorothioate DNA oligonucleotides were synthesized according to the procedure set forth in Examples 1 and 2 respectively, replacing the standard oxidation bottle by a 0.2M solution of 3H-1,2-benzodithiole-3-one 1,1-dioxide in acetonitrile for stepwise thiation of phosphite linkages. The thiation cycle wait step was increased to 68 seconds and is followed by the capping step.

EXAMPLE 4

Synthesis of 2'-O-alkyl Phosphorothioate Oligonucleotides

2'-O-methyl phosphorothioate oligonucleotides were synthesized according to the procedures set forth in Example 3 substituting 2'-O-methyl β-cyanoethyldiisopropyl phosphoramidites (Chemgenes, Needham, Mass.) for standard phosphoramidites and increasing the wait cycle after the pulse delivery of tetrazole and base to 360 seconds. Similarly, 2'-O-phenyl, 2'-O-propyl and other 2'-O-alkyl phosphorothioate oligonucleotides may be prepared by slight modifications of this procedure.

EXAMPLE 5

Preparation of Pyrene Oligonucleotide Analogs

Oligonucleotides were prepared by incorporating 2' aminopentoxyadenosine at desired sites. The oligonucleotides were dissolved in 0.2M $NaHCO_3$ buffer and treated with 50-fold excess of N-hydroxysuccinimide ester of pyrene-1-butyric acid dissolved in dimethylformamide. The resultant mixture is incubated at 37° C. for 4–5 hours and the conjugate is purified by reverse phase HPLC followed by desalting in a G-25 Sephadex column.

EXAMPLE 6

Synthesis of Oligonucleotide Pools Having Randomized Positions

Four columns of the DNA synthesizer were packed with a mixture containing an equal amount of adenosine(A)-, cytidine(C)-, guanosine(G)- and thymidine(T)- or uridine (U)-controlled pore glass (CPG, Chemgenes, Needham, Mass.). At coupling steps where a given nucleotide base was desired, the defined phosphoramidite was delivered to each column. At each "random" coupling step, an equimolar mixture of all four phosphoramidites was delivered to each column.

EXAMPLE 7

Preparation of Radiolabeled Groups

Oligonucleotide groups prepared in accordance with Example 1 through 6 are radiolabeled using $[\gamma^{-32}P]$ ATP and T4 polynucleotide kinase as described in Sambrook et al., *Molecular Cloning. A Laboratory Manual*, Cold Spring Harbor Laboratory Press, 1989, Volume 2, pg. 11.31–11.32.

EXAMPLE 8

Preparation of Oligonucleotide Group comprising Nucleotide Analogs.

Oligonucleotide groups are prepared in accordance with Example 1 and 6 incorporating one or more of the nucleoside analogs 2'-O-nonyl adenosine, 6-N-imidazoylpropyl guanosine, 2'-O-aminopentyl cytidine, 2'-O-pentyl-adenosine, 2'-O-pentyl-guanosine, 2'-O-pentyl-cytidine, 3'-terminal 2'-O-methyl uridine and 6-amino-2-hydroxylmethyl-1-hexanol. The nucleosides, 2'-O-nonyl adenosine, N6-imidazoylpropyl guanosine, 2'-O-aminopentyl cytidine, 2'-O-pentyl-adenosine, 2'-O-pentyl-guanosine, 2'-O-pentyl-cytidine, 3'-terminal 2'-O-methyl uridine were prepared by modification of the methods described in PCT US91/00243 filed Jan. 11, 1991. 6-amino-2-hydroxylmethyl-1-hexanol is available commercially. The nucleosides are modified to provide the corresponding phosphoramidite by methods known to those skilled in the art.

EXAMPLE 9

Gel Shift assay of Random DNA Oligonucleotide Binding to ras RNA Target and Enzymatic Amplification of Active Oligonucleotides The ras 47-mer stem/loop RNA was enzymatically synthesized, $^{32}$P end-labeled according to standard procedures, and gel-purified. The ras target is incubated at a concentration of approximately 10–50 pM with DNA oligonucleotide pools synthesized in accordance with the method described in Examples 1 and 6 at concentrations of 1, 5, 10, 50 and 100 µM in a buffer consisting of 100 mM NaCl and 10 mM MgCl$_2$. The hybridization is carried out for four hours at 37° C., followed by electrophoresis separation of bound vs. unbound material on a 20% polyacrylamide gel in Tris-Borate buffer (TBE) plus 50 mM NaCl run at 25 W for four hours. The gel is dried and the radioactive bands are visualized on a phosphorimager (Molecular Dynamics). The ras stem/loop target alone will be the lowest band visible on the gel (highest mobility). As this target binds oligonucleotide (non-radioactive), the mobility of the ras target will decrease, shifting the band to a higher position on the gel (complex). The bound complex is excised from the gel with a sterile razor blade. The oligonucleotides (ras RNA and bound oligonucleotide(s)) are recovered by the crush and soak method. The ras RNA and binding selected oligonucleotide(s) are separated by size using HPLC procedures and the fraction(s) containing the binding selected oligonucleotides collected. The recovered oligonucleotides are amplified in accordance with the following steps:

(1) Poly dA tailing of recovered oligonucleotides to form a first strand

Tailing of recovered oligonucleotides is carried out in a microtitre well using 5–50 units terminal deoxynucleotide transferase (Boehringer Mannheim Biochemicals) according to manufacturer's instructions [2 hours, 37° C. in tailing buffer (supplied with enzyme) plus 1.5 mM CoCl$_2$ and 100 nM dATP]. Reaction volume is 20 µl.

(2) Preparation of a first chimeric primer

A first chimeric primer is synthesized by automated chemical synthesis. At the 5' end is a known sequence incorporating a ribonuclease restriction site for FokI and a biotin moiety at the 5' termini. At the 3' end is a 13 nucleotide polydT stretch. This primer is added at micromolar concentrations to the reaction mixture in a buffer consisting of 10 mM Tris-HCl, pH 7.5, 150 mM NaCl and allowed to hybridize to the first strand.

(3) Capture of the first chimeric primer with 5'-biotin-streptavidin

A microtitre well is coated with 50 µg/ml streptavidin in sodium carbonate, pH 9.25 for 3 hours at 37° C. Alternatively, commercially available streptavidin ready-coated microtitre plates (Labsystems, Marlboro, Mass.) can be used. Nonspecific binding sites are blocked with 0.3% bovine serum albumin in 10 mM Tris-HCl, pH 8.0, 150 mM NaCl at 37° C. for 3 hours. The first chimeric primer/oligonucleotide duplex is then bound to the streptavidin-coated plates by incubating for 1 hour at 37° C. in 100 mM Tris-HCl, 150 mM NaCl, pH 8.0.

(4) Polymerase copy of first strand to form double-stranded duplex:

To the microtitre well is added 0.4 units Taq polymerase (Promega), micromolar amounts of each dNTP, and 1x polymerase buffer (Promega) to a final volume of 50 µl. The reaction is carried out for 3 to 12 hours at room temperature. Well are washed six times in wash buffer.

(5) Poly-dA tailing of cDNA of duplex

Tailing of the cDNA is carried out in a microtitre well using 5–50 units terminal deoxynucleotide transferase (Boehringer Mannheim Biochemicals) according to manufacturer's instructions [2 hours, 37° C. in tailing buffer (supplied with enzyme) plus 1.5 mM CoCl$_2$ and 100 nM dATP]. Well is washed 6 times with 200 µl of wash buffer.

(6) Separation of cDNA and oligonucleotide

The microtitre plate is heated to 85° C. to melt the duplex and the supernatant is removed. The well is washed six times with 200 µl wash buffer.

(7) Preparation of a second chimeric primer

A second chimeric primer is synthesized by automated chemical synthesis. At the 5' end is a known sequence incorporating a ribonuclease restriction site for BamH1. At the 3' end is a 14 nucleotide polydT stretch ending in a riboU at its termini. This primer is added at micromolar concentrations to the reaction mixture in a buffer consisting of 10 mM Tris-HCl, pH 7.5, 150 mM NaCl and allowed to hybridize to the first strand.

(8) Filling in recessed ends to form a duplex

To the microtitre well is added 0.4 units Taq polymerase (Promega), micromolar amounts of each dNTP, and 1x polymerase buffer (Promega) to a final volume of 50 µl. The reaction is carried out for 3 to 12 hours at room temperature. Wells are washed six times in wash buffer. The microtitre plate is heated to $\geq 85°$ C. to melt the duplex.

(9) PCR Amplification of Oligonucleotides

PCR amplification is performed using Taq polymerase according to standard methods (Frederick M. Ausubel et al., *Current Protocols in Molecular Biology*, John Wiley and Sons, 1989) using first and second chimeric primers from (2) and (7) as PCR primers.

(10) Excising oligonucleotide from upstream and downstream flanking regions

Amplified oligonucleotides are excised from flanking regions by cleavage with FokI in accordance with suppliers recommendations (Boehringer Mannheim). After FokI restriction and melting apart of the restricted sense and antisense fragments, the reaction mixture was treated with mild base to cleave the upstream primer region from the sense strand by selective hydrolysis of the ribophosphate diester linkage between the 3'-riboU of the primer and the 5' region of the oligonucleotide of interest.

(11) The selection steps and amplification steps are repeated until only one, or at most only a few, unique oligonucleotide sequences reproducible are recovered from "round to round".

(12) Sequencing of amplified oligonucleotide(s):

The sequence is determined using the standard Sanger ddNTP method and Sequence enzyme (Pharmacia, Inc.) (Frederick M. Ausubel et al., *Current Protocols in Molecular Biology*, John Wiley and Sons, 1989). Sequencing can be done with one, two, three, or all four ddNTPs, depending on the extent of sequence bias, or if exact sequence is desired.

EXAMPLE 10

Gel Shift assay of Random 2'-O-Methyl Oligonucleotide Binding to ras RNA Target and Microanalytical Characterization The ras 47-mer stem/loop RNA was enzymatically synthesized, $^{32}P$ end-labeled according to standard procedures, and gel-purified. The ras target is incubated at a concentration of approximately 10-50 pM with random 2'-O-methyl oligonucleotide pools synthesized in accordance with the method described in Examples 4 and 6 at concentrations of 1, 5, 10, 50 and 100 μM in a buffer consisting of 100 mM NaCl and 10 mM $MgCl_2$. The hybridization is carried out for four hours at 37° C., followed by electrophoresis separation of bound vs. unbound material on a 20% polyacrylamide gel in Tris-Borate buffer (TBE) plus 50 mM NaCl run at 25 W for four hours. The gel is dried and the radioactive bands are visualized on a phosphorimager (Molecular Dynamics). The ras stem/loop target alone will be the lowest band visible on the gel (highest mobility). As this target binds oligonucleotide (non-radioactive), the mobility of the ras target will decrease, shifting the band to a higher position on the gel (complex). The bound complex is excised from the gel with a sterile razor blade. The oligonucleotides (ras RNA and bound oligonucleotide(s)) are recovered by crush and soak method or by electroelution. The ras RNA and binding selected oligonucleotide(s) are separated by RNase degradation which selectively degrades the ras RNA to mononucleotides, leaving the selected, RNase resistant 2'-O-methyl oligonucleotide(s) intact. The selected oligonucleotides are identified by the use of microbore HPLC and mass spectrometry to determine the bound oligonucleotide sequences. To facilitate MS sequencing determination, the recovered 2'-O-methyl oligonucleotide(s) can be fragmented by prolonged treatment (compared to RNA or DNA) with any of a number of available nucleases; sequencing of shorter fragments by MS is easier and the sequence of the parent oligonucleotide can be reconstructed from overlapping sequences of the fragments.

EXAMPLE 11

Gel Shift Assay of Random Pyrene Oligonucleotide Sets Binding to HIV TAR Element The HIV TAR element is a structured RNA found on the 5'-end of all HIV transcripts. A gel shift is used to analyze the binding of oligonucleotides of a random oligonucleotide pool prepared in accordance with Examples 5 and 6, each oligonucleotide pool containing a pyrene analog to the HIV TAR element. The target RNA has a three base bulge that is required for binding of the transcriptional activation protein tat. The assay uses a very low concentration of pools. Binding of molecules from the pool to the target results in a slower mobility complex. Recovery of the bound oligonucleotide(s) and identification of sequences can be accomplished as described in Example 10.

EXAMPLE 12

Random 2'-O-Methyl Oligonucleotide Binding to ras RNA using Continuous Flow Mass Transport Methodology to Effect Stringent Binding Selection The ras 47-mer stem/loop RNA was enzymatically synthesized, $^{32}P$ end-labeled according to standard procedures, and gel-purified.

A fast protein liquid chromatography (FPLC, Pharmacia) system is calibrated to separate bound from unbound oligonucleotides. The column used is a Superous 12 HR 10/30, fractionation MW range of $10^3-3\times10^5$ (for proteins), >40,000 theoretical plates/m, 1.0×30 cm, with ≦6–30 mL/min flow rate. Starting conditions are 10–50 mM TE buffer, pH 7.0, 1 mM magnesium chloride and 100 mM sodium chloride.

Calibration 2'-O-methyl oligonucleotides having the sequences UUGCCCACAC (SEQ ID NO:3), UUGCCCACAU (SEQ ID NO:4), UUGCUCACAC (SEQ ID NO:5), CUGCCCACAU (SEQ ID NO:6), and CUGUUUACAU (SEQ ID NO:7) are prepared and radiolabeled using polynucleotide kinase and $^{32}P$-ATP. Alternatively, rather than label the oligonucleotides, the target molecule, ras RNA may be $^{32}P$ labeled or both oligonucleotide and target may be labeled. These calibration oligonucleotides should be of the same length as the randomized oligonucleotides to be tested and are of varying degrees of sequence complementarity to the target molecule.

The FPLC column is calibrated before antisense selection from combinatorial pools by running the calibration $^{32}P$ labeled-2'-O-methyl oligonucleotides; individually (for unbound species retention times (RT)) and as a mixture of calibration 2'-O-methyl oligonucleotides which has been incubated with ras RNA to form any possible hybridization complexes (for retention times of bound and differential rate dissociated species). The mixture is then loaded on the column and run to provide an elution profile. Alternatively, the calibration oligonucleotides may be added to the column as a mixture, followed by the addition of the ras RNA. As the ras RNA should flow faster than the oligonucleotides, it should flow past the oligonucleotides. This continuous flow combining binding and resolution may allow for better separation and recovery because the mass action bulk equilibrium starting point of pre-binding is to some extent avoided. The effect of adding a weak, nonspecific binder of oligonucleotides in mass excess in the mobile phase can similarly be assessed.

Following calibration, either the random oligonucleotide pool is loaded onto the column followed by the ras RNA or the pool and ras RNA are pre-incubated (37° C., 1–4 hours) prior to loading on the column. Bound oligonucleotide/ras RNA complex(es) are dissociated using stepwise or gradient low salt and/or increased temperature and the oligonucleotides are recovered by RNAse treatment to selectively degrade the ras RNA. The selected 2'-O-methyl oligonucleotides are characterized by microbore HPLC (Smart Systems from Pharmacia). Complete and limited fragmentation of the recovered 2'-O-methyl oligonucleotides can be

EXAMPLE 13

FPLC resolution of Random RNA Oligonucleotide Binding to ras RNA

The ras 47-mer stem/loop RNA is enzymatically synthesized, is biotin-labeled according to standard procedures, and gel-purified. Calibration oligonucleotides were prepared and FPLC system calibrated as described in Example 12. An RNA random oligonucleotide pool was prepared in accordance with Examples 2 and 6 and the FPLC binding assay was performed as described in Example 12. The RNA-oligonucleotide(s) bound complex(es) were recovered using biotin-streptavidin capture of the biotinylated ras RNA. The bound oligonucleotide(s)/ras RNA complex(es) are dissociated using low salt and/or increased temperature and the selected oligonucleotide(s) recovered from the supernatant. The oligonucleotide was amplified according to a modification of the procedure in Example 9.

EXAMPLE 14

In Vitro Evolution of Longer Oligonucleotides of Greater Complexity for Enhanced Binding Affinity and Specificity A "winner" sequence is determined in accordance with one of the Examples 9–13. The "winner" sequence is designated a cassette for purposes of the invention, i.e. an oligonucleotide sequence determined by an initial application of methods of the invention.

In subsequent application of methods of the invention a randomized oligonucleotide pool is prepared in accordance with Example 1 comprising the previously determined cassette and at least one randomized flanking region. Selection for activity is performed and the oligonucleotide characterized as described in Examples 10–14. These steps can be performed iteratively. Thus, the final sequence may subsequently be used as a cassette in order to expand upon the known desired sequence to optimize selective activity.

EXAMPLE 15

Identification of Oligonucleotide Sequence Using Streptavidin Capture of Biotinylated Target A target oligonucleotide (0.2 µM) having the sequence 3' dBAB AGA CGT CTT GCG 5' (SEQ ID NO:8) wherein B is biotin, was incubated for 30 minutes at room temperature with a radiolabeled 2'-O-methyl oligonucleotide sequence randomized pool (10 µM) having the sequence NNNNC-NCNN wherein N is any of adenine, cytosine, thymine or guanine. The target oligonucleotide was captured on streptavidin-coated magnetic beads (Promega), the beads were washed, and supernatant removed. The bead-containing sample was run on polyacrylamide gel to determine the sample having the highest binding. The binding selective steps were repeated until a winner sequence was identified. Enrichment in each step (measured by radioactivity) was 200- to 1000-fold. Confirmation of the sequence of the final, best binding oligonucleotide was provided by complete blocking of binding of radioactivity by 0.1 µM of unlabeled target complementary to the sequence competitor.

EXAMPLE 16

Identification of a Protein Target

A group of oligonucleotides having the sequence NNNNNNNN wherein N is any one of adenine, guanine, thymidine or cytosine is prepared in accordance with Example 3. The group is labeled using [$\gamma$-$^{32}$P]ATP and T4 polynucleotide kinase.

In individual wells of a 96-well nitrocellulose filter manifold, the following proteins are incubated in a solution of phosphate buffered saline: plasminogen activator $A_2$, tumor necrosis factor $\alpha$, tumor necrosis factor $\beta$ and gp120. Phosphate buffered saline only is added to a control well. The filter is washed. An aliquot of the labeled group of oligonucleotides is added to each well and incubated at room temperature for 10 minutes. The filter is washed and the counts in each well over background are counted to determine whether binding of the oligonucleotide to the protein occurred.

EXAMPLE 17

RNase H affinity mapping of ras RNA by RNAse H cleavage mapping

The ras 47-mer stem/loop RNA was enzymatically synthesized, $^{32}$p end-labeled according to Sambrook et al., *Molecular Cloning. A Laboratory Manual*, Cold Spring Harbor Laboratory Press, 1989, Volume 2, pg. 11.31–11.32, and gel-purified. The ras target was incubated at a concentration of approximately 1 µM to 10 nM with random oligonucleotide pools synthesized in accordance with the method described in Example 1 at individual oligonucleotide concentrations of 100 pM in 10 mM Tris buffer (pH 8) containing 50 mM NaCl and 5 mM $MgCl_2$. The hybridization was carried out for at least 16 hours at 37° C. RNase H (1 U/µL) was added in 1:10 to 1:1000 dilutions, incubated at 37° C. for 10 minutes, and quenched by snap freezing. A "G" map, using RNase T1, and base ladder, using 50 mM $Na_2CO_3$ buffer (pH 9), were prepared. The digestion products were resolved by sequencing polyacrylamide gel electrophoresis (PAGE). This method provided information regarding the preferred hybridization sites for oligonucleotides on the target ras RNA. Preferred hybridization sites are shown in Table II.

TABLE II

| | Target sites identified by RNase H affinity mapping | |
|---|---|---|
| Target Site | SEQ ID NO: | Sequence |
| 1 | 9 | UGGUGGGCGC |
| 2 | 10 | GGCAAGAGUG |
| 3 | 11 | CGUCGGUGUG |
| 4 | 12 | GUCGGUGUGG |

EXAMPLE 18

RNase H affinity mapping of HCV RNA by RNAse H cleavage mapping

The 5'-untranslated region (UTR) of Hepatitis C virus (HCV) was enzymatically synthesized as two transcript fragments of 370 and 200 nucleotides. These transcripts overlap by 130 nucleotides, and together encompass the entire 5'-UTR of HCV. The two transcripts were $^{32}$P end-labeled according to Sambrook et al., *Molecular Cloning. A*

*Laboratory Manual*, Cold Spring Harbor Laboratory Press, 1989, Volume 2, pg. 11.31–11.32, and gel-purified. Each transcript comprising the 5'-UTR was incubated at a concentration of approximately 1 µM to 10 nM with random oligonucleotide pools synthesized in accordance with the method described in Example 1 at individual oligonucleotide concentrations of 100 pM in 10 mM Tris buffer (pH 8) containing 50 mM NaCl and 5 mM $MgCl_2$. The hybridization was carried out for at least 16 hours at 37° C. RNase H (1 U/µL) was added in 1:10 to 1:1000 dilutions, incubated at 37° C. for 10 minutes, and quenched by snap freezing. A "G" map, using RNase T1, and base ladder, using 50 mM $Na_2CO_3$ buffer (pH 9), were prepared. The digestion products were resolved by sequencing polyacrylamide gel electrophoresis (PAGE) in order to identify preferred hybridization sites of oligonucleotides on each of the HCV RNA transcripts. The preferred hybridization site information was then used to synthesize complementary oligonucleotides which bind to this site in order to optimize their binding to the target RNA.

EXAMPLE 19

"RNase ONE" footprinting assay with HCV RNA

Two transcript fragments (370 and 200 nucleotides in length, which overlap by 200 nucleotides) that encompass the entire 5'-untranslated region (5'-UTR) of Hepatitis C virus (HCV) were incubated at a concentration of 3–30 pM with oligonucleotides that were complementary to the preferred hybridization sites on the target. These oligonucleotides were synthesized in accordance with the method described in Example 1 at a concentration of 10 µM in 10 mM Tris buffer (pH 8) containing 50 mM NaCl and 5 mM $MgCl_2$. The hybridization was carried out for at least 16 hours at 37° C. "RNase ONE" (10 U/µL, Promega) was added in 1:2000 to 1:100,000 dilutions, incubated at 25° C. for 5 minutes, and quenched by snap freezing. A "G" map, using RNase T1, and base ladder, using 50 mM $Na_2CO_3$ buffer (pH 9), were prepared. The digestion products were resolved by sequencing PAGE in order to identify at least one oligonucleotide that exhibits an "RNase ONE" footprint at 10 µM. The $K_d$ for an oligonucleotide of interest was then determined by titrating that oligonucleotide, at concentrations ranging from 100 pM to 10 µM, with "RNase ONE". The digestion products were separated by sequencing PAGE and the percent protection afforded by the oligonucleotide was plotted as a function of the oligonucleotide concentration. The concentration of oligonucleotide at which 50% protection is observed is the $K_d$ for that oligonucleotide of interest. Using this method, oligonucleotides with optimal binding and specificity for the target HCV RNA were identified. The $K_d$ values, base sequences and sequence ID numbers for these oligonucleotides are shown in Table III.

TABLE III

| Oligonucleotides having preferred hybridization sites on HCV RNA | | |
|---|---|---|
| SEQUENCE | $K_d$ (M) | SEQ ID NO: |
| GAT CTA TGG T | $1 \times 10^{-8}$ | 13 |
| GTG ATC TAT G | $5 \times 10^{-7}$ | 14 |

EXAMPLE 20

"RNase ONE" footprinting assay with ras RNA

The ras 47-mer stem/loop RNA was incubated at a concentration of 3–30 pM with oligonucleotides that were complementary to the preferred hybridization sites on the target. These oligonucleotides were synthesized in accordance with the method described in Examples 1 and 2, or with commercially available (Glen Research) 2'-O-methyl amidites, at a concentration of 10 µM in 10 mM Tris buffer (pH 8) consisting of 50 mM NaCl and 5 mM $MgCl_2$. The hybridization was carried out for at least 16 hours at 37° C. "RNase ONE" (10 U/µL, Promega) was added in 1:2000 to 1:100,000 dilutions, incubated at 25° C. for 5 minutes, and quenched by snap freezing. A "G" map, using RNase T1, and base ladder, using 50 mM $Na_2CO_3$ buffer (pH 9), were prepared. The digestion products were resolved by sequencing PAGE in order to identify at least one oligonucleotide that exhibits an "RNase ONE" footprint at 10 µM. The $K_d$ for an oligonucleotide of interest was then determined by titrating that oligonucleotide, at concentrations ranging from 100 pM to 10 µM, with "RNase ONE". The digestion products were separated by sequencing PAGE and the percent protection afforded by the oligonucleotide was plotted as a function of the oligonucleotide concentration. The concentration of oligonucleotide at which 50% protection is observed is the $K_d$ for that oligonucleotide of interest. Using this method, oligonucleotides with enhanced affinity and specificity for the target ras RNA were identified. The $K_d$ values, base sequences and sequence ID numbers for these oligonucleotides are shown in Table IV.

TABLE IV

| Oligonucleotides having preferred hybridization sites on ras RNA | | | |
|---|---|---|---|
| ISIS # | SEQUENCE | $K_d$ (M) | SEQ ID NO: |
| 3271 | GCG CCC ACC A | $1 \times 10^{-6}$ | 15 |
| 3284 | CAC UCU UGC C | $0.33 \times 10^{-5}$ | 16 |
| 3291 | CAC ACC GAC G | $0.33 \times 10^{-10}$ | 17 |
| 4272 | CCA CAC CGA C | $0.33 \times 10^{-10}$ | 18 |

EXAMPLE 21

Affinity mapping of HIV RNA by RNase H cleavage mapping

The HIV RNA transcripts (rev, tar and 5' long terminal repeat regions) were enzymatically synthesized, $^{32}P$ end-labeled according to Sambrook et al., *Molecular Cloning. A Laboratory Manual*, Cold Spring Harbor Laboratory Press, 1989, Volume 2, pg. 11.31–11.32, and gel-purified. The HIV target was incubated at a concentration of approximately 1 µM to 10 nM with random oligonucleotide pools synthesized in accordance with the method described in Example 1 at individual oligonucleotide concentrations of 100 pM in 10 mM Tris buffer (pH 8) containing 50 mM NaCl and 5 mM $MgCl_2$. The hybridization was carried out for at least 16 hours at 37° C. RNase H (1 U/µL) was added in 1:10 to 1:1000 dilutions, incubated at 37° C. for 10 minutes, and quenched by snap freezing. A "G" map, using RNase T1, and base ladder, using 50 mM $Na_2CO_3$ buffer (pH 9), were prepared. The digestion products were resolved by sequencing polyacrylamide gel electrophoresis (PAGE). This method provided information regarding the preferred hybridization sites for oligonucleotides on the target HIV RNA, and are shown in Table VI.

TABLE VI

| Target sites identified on HIV RNA by RNase H affinity mapping | |
|---|---|
| Target Site | Sequence |
| 1 | GAAG |
| 2 | AGGA |
| 3 | GCAG |
| 4 | GGCA |
| 5 | GAGAG |
| 6 | GCCCG |

---

What is claimed is:

1. A method of determining an oligonucleotide having specific activity for a target biomolecule comprising the steps of:
   (a) preparing a set of randomized oligonucleotides;
   (b) subfractionating the set of randomized oligonucleotides to provide subfractions of said oligonucleotides;
   (c) assaying the subfractions of randomized oligonucleotides for activity against a target biomolecule;
   (d) selecting the subfraction having the highest activity;
   (e) assaying the oligonucleotides of the selected subfraction for activity against a target biomolecule;
   (f) separating active from inactive oligonucleotides;
   (g) recovering said active oligonucleotides;
   (h) extending a polyA on said active oligonucleotide in a 3' direction to form a first strand;
   (i) hybridizing said first strand to a first chimeric primer having a 5' known sequence and a 3' polydT portion
   (j) forming a cDNA strand, complementary to the active oligonucleotide, using the first chimeric primer;
   (k) extending said cDNA formed in (j) in a 3' direction by the addition of polyA;
   (l) separating said oligonucleotide and cDNA strand;
   (m) hybridizing the polyA portion of said cDNA strand to a second chimeric primer having a 5' known sequence and a 3' polydT portion;
   (n) filling in the recessed 3' ends to form two complementary strands;
   (o) separating the strands;
   (p) amplifying the strands formed in (n) using the first and second chimeric primers by polymerase chain reaction;
   (q) excising active oligonucleotide from flanking regions;
   (r) recovering active oligonucleotide; and
   (s) performing steps (b) through (r) iteratively to determine an active oligonucleotide.

2. The method of claim 1 further comprising determining the nucleic acid sequence of the active oligonucleotide.

3. The method of claim 1 wherein the biomolecule is a DNA molecule.

4. The method of claim 1 wherein the biomolecule is an RNA molecule.

5. The method of claim 1 wherein the biomolecule is polypeptide.

6. The method of claim 1 wherein the biomolecule is a glycoprotein.

7. The method of claim 1 wherein the biomolecule is a carbohydrate.

8. The method of claim 1 wherein the set of randomized oligonucleotides is detectably labeled.

9. The method of claim 1 wherein the set of randomized oligonucleotides is conformationally constrained.

10. A method of determining an oligonucleotide having specific activity for a target biomolecule comprising the steps of:
 (a) preparing a set of randomized oligonucleotides;
 (b) assaying the set of randomized oligonucleotides for activity against a target biomolecule;
 (c) separating active from inactive oligonucleotides;
 (d) recovering active oligonucleotide;
 (e) extending a polyA on said active oligonucleotide in a 3' direction to form a first strand;
 (f) hybridizing said first strand to a first chimeric primer having a 5' known sequence and a 3' polydT portion.
 (g) forming a cDNA strand, complementary to active oligonucleotide, using the first chimeric primer;
 (h) extending said cDNA formed in (g) in a 3' direction by the addition of polyA;
 (i) separating said oligonucleotide and cDNA strand;
 (j) hybridizing the polyA portion of said cDNA strand to a second chimeric primer having a 5' known sequence and a 3' polydT portion;
 (k) filling in the recessed 3' ends to form two complementary strands;
 (l) separating the strands;
 (m) amplifying the strands formed in (k) using the first and second chimeric primers by polymerase chain reaction;
 (n) excising active oligonucleotide;
 (o) recovering active oligonucleotide; and
 (p) performing steps (b) through (o) iteratively to determine an oligonucleotide having specific activity for a target biomolecule.

11. The method of claim 10 further comprising determining the nucleic acid sequence of the active oligonucleotide.

12. The method of claim 10 wherein the biomolecule is a DNA molecule.

13. The method of claim 10 wherein the biomolecule is an RNA molecule.

14. The method of claim 10 wherein the biomolecule is polypeptide.

15. The method of claim 10 wherein the biomolecule is a glycoprotein.

16. The method of claim 10 wherein the biomolecule is a carbohydrate.

17. The method of claim 10 wherein the set of randomized oligonucleotides is detectably labeled.

18. The method of claim 10 wherein the set of randomized oligonucleotides is conformationally constrained.

19. A method for determining an oligonucleotide having specific activity for a target biomolecule comprising the steps of:
 (a) preparing a set of randomized oligonucleotides;
 (b) subfractionating the set of randomized oligonucleotides to provide subfractions of said oligonucleotides;
 (c) assaying each of the subfractions of randomized oligonucleotides for activity against a target biomolecule;
 (d) selecting the subfraction having the highest activity;
 (e) assaying the oligonucleotides of the selected subfraction for activity against a target biomolecule;
 (f) separating active from inactive oligonucleotides;
 (g) recovering said active oligonucleotides;
 (h) amplifying the active oligonucleotides recovered in (d); and
 (i) determining the nucleic acid sequence of said amplified oligonucleotides.

20. The method of claim 19 wherein the biomolecule is a DNA molecule.

21. The method of claim 19 wherein the biomolecule is an RNA molecule.

22. The method of claim 19 wherein the biomolecule is polypeptide.

23. The method of claim 19 wherein the biomolecule is a glycoprotein.

24. The method of claim 19 wherein the biomolecule is a carbohydrate.

25. The method of claim 19 wherein the set of randomized oligonucleotides is detectably labeled.

26. The method of claim 19 wherein the set of randomized oligonucleotides is conformationally constrained.

27. A method of determining an oligonucleotide having specific activity for a target biomolecule comprising the steps of:
 (a) preparing a set of randomized oligonucleotides;
 (b) assaying the set of randomized oligonucleotides for activity against a target biomolecule;
 (c) separating active from inactive oligonucleotides;
 (d) recovering said active oligonucleotides;
 (e) amplifying the active oligonucleotides; and
 (f) determining the nucleic acid sequence of said amplified oligonucleotides.

28. The method of claim 27 wherein the biomolecule is a DNA molecule.

29. The method of claim 27 wherein the biomolecule is an RNA molecule.

30. The method of claim 27 wherein the biomolecule is polypeptide.

31. The method of claim 27 wherein the biomolecule is a glycoprotein.

32. The method of claim 27 wherein the biomolecule is a carbohydrate.

33. The method of claim 27 wherein the set of randomized oligonucleotides is detectably labeled.

34. The method of claim 27 wherein the set of randomized oligonucleotides is conformationally constrained.

35. A method of determining an oligonucleotide having specific activity for a target biomolecule comprising the steps of:
 (a) preparing a set of randomized oligonucleotides;
 (b) assaying the set of randomized oligonucleotides for activity against a target biomolecule;
 (c) separating active from inactive oligonucleotides;
 (d) recovering said active oligonucleotides;
 (e) characterizing the recovered oligonucleotides to provide an oligonucleotide having specific activity for said target biomolecule;

(f) preparing a set of oligonucleotides comprising an oligonucleotide of the previous characterizing step and at least one flanking region of randomized positions;

(g) assaying the set of oligonucleotides for activity against a target biomolecule;

(h) separating active from inactive oligonucleotides;

(i) recovering said active oligonucleotides;

(j) characterizing the recovered oligonucleotides to provide an oligonucleotide having specific activity for said target biomolecule; and (k) performing steps (f) through (j) iteratively to determine an oligonucleotide having specific activity for a target biomolecule.

36. The method of claim 35 wherein the active and inactive oligonucleotides are separated by microanalytical techniques.

37. The method of claim 35 wherein the recovered oligonucleotides are characterized by microanalytical structural determination or by amplifying the active oligonucleotides and determining the nucleic acid sequence of said amplified oligonucleotides.

38. A method for determining an oligonucleotide having specific activity for a target biomolecule comprising the steps of:

(a) preparing a set of randomized oligonucleotides;

(b) subfractionating the set of randomized oligonucleotides to provide subfractions of said oligonucleotides;

(c) assaying each of the subfractions of randomized oligonucleotides for activity against a target biomolecule;

(d) selecting the subfraction having the highest activity;

(e) assaying the oligonucleotides of the selected subfraction for activity against a target biomolecule;

(f) separating active from inactive oligonucleotides;

(g) recovering said active oligonucleotides; and (h) characterizing the recovered oligonucleotides by microanalytical structural determination.

39. The method of claim 38 wherein said microanalytical structural determination is mass spectrometry.

40. The method of claim 38 wherein the biomolecule is a DNA molecule.

41. The method of claim 38 wherein the biomolecule is an RNA molecule.

42. The method of claim 38 wherein the biomolecule is polypeptide.

43. The method of claim 38 wherein the biomolecule is a glycoprotein.

44. The method of claim 38 wherein the biomolecule is a carbohydrate.

45. The method of claim 38 wherein the set of randomized oligonucleotides is detectably labeled.

46. The method of claim 38 wherein the set of randomized oligonucleotides is conformationally constrained.

47. A method of determining an oligonucleotide having specific activity for a target biomolecule comprising the steps of:

(a) preparing a set of randomized oligonucleotides;

(b) assaying the set of randomized oligonucleotides for activity against a target biomolecule;

(c) separating active from inactive oligonucleotides;

(d) recovering said active oligonucleotides; and (e) characterizing the recovered oligonucleotides by microanalytical structural determination.

48. The method of claim 47 wherein said microanalytical structural determination is mass spectrometry.

49. The method of claim 47 wherein the biomolecule is a DNA molecule.

50. The method of claim 47 wherein the biomolecule is an RNA molecule.

51. The method of claim 47 wherein the biomolecule is polypeptide.

52. The method of claim 47 wherein the biomolecule is a glycoprotein.

53. The method of claim 47 wherein the biomolecule is a carbohydrate.

54. The method of claim 47 wherein the set of randomized oligonucleotides is detectably labeled.

55. The method of claim 47 wherein the set of randomized oligonucleotides is conformationally constrained.

56. An oligonucleotide identified in accordance with the method of claim 1.

57. An oligonucleotide identified in accordance with the method of claim 10.

58. An oligonucleotide identified in accordance with the method of claim 19.

59. An olmgonucieotide identified in accordance with the method of claim 27.

60. An oligonucleotide identified in accordance with the method of claim 35.

61. An oligonucleotide identified in accordance with the method of claim 38.

62. An oligonucleotide identified in accordance with the method of claim 47.

63. A method of determining an oligonucleotide having specific activity for a target nucleic acid biomolecule comprising the steps of:

(a) preparing a set of randomized oligonucleotides;

(b) assaying the set of randomized oligonucleotides for activity against said target nucleic acid biomolecule;

(c) determining the nucleic acid sequence of the target region of said target nucleic acid biomolecule to which the active oligonucleotides bind; and (d) deducing the sequence of the oligonucleotides which are complementary to said target region.

64. The method of claim 63 wherein the target nucleic acid molecule is Hepatitis C virus RNA.

65. The method of claim 63 wherein the target nucleic acid molecule is ras RNA.

66. The method of claim 63 wherein the target nucleic acid molecule is HIV RNA.

67. The method of claim 63 wherein the nucleic acid sequence of the target region to which the active oligonucleotides bind is determined by cleavage mapping.

68. The method of claim 67 wherein mapping is done using enzymatic cleavage.

69. The method of claim 68 wherein the enzymatic cleaver is RNase H.

70. The method of claim 67 wherein mapping is done using chemical cleavage.

71. The method of claim 63 further comprising the steps of:

(e) preparing oligonucleotides which are complementary to the target region in (c); and (f) determining which of these sequences has the greatest specific activity for the target nucleic acid biomolecule.

72. The method of claim 71 further comprising the steps of:

(g) determining the $K_d$ of the oligonucleotides in (e); and (h) choosing the oligonucleotide with the lowest $K_d$.

73. The method of claim 71 wherein the binding of the oligonucleotides to the target nucleic acid biomolecule is optimized by "RNase ONE" footprinting.

74. The method of claim 72 wherein the binding of the oligonucleotides to the target nucleic acid biomolecule is optimized by "RNase ONE" footprinting.

75. The method of claim 72 wherein the $K_d$ of the tightest binding oligonucleotides are determined by titrating with "RNase ONE".

76. The method of claim 71 wherein the oligonucleotides are oligoribonucleotides or oligodeoxyribonucleotides.

77. The method of claim 72 wherein the oligonucleotides are oligoribonucleotides or oligodeoxyribonucleotides.

* * * * *

UNITED STATES PATENT AND TRADEMARK OFFICE
CERTIFICATE OF CORRECTION

PATENT NO. : 5,686,242
DATED : November 11, 1997
INVENTOR(S) : Bruice et al.

It is certified that error appears in the above-identified patent and that said Letters Patent is hereby corrected as shown below:

Column 38, claim 59, please delete "olmgonucieotide" and insert therefor --oligonucleotide--.

Signed and Sealed this

Twenty-eighth Day of July, 1998

Attest:

Attesting Officer

BRUCE LEHMAN

Commissioner of Patents and Trademarks